US010400177B2

(12) United States Patent
Le et al.

(10) Patent No.: US 10,400,177 B2
(45) Date of Patent: *Sep. 3, 2019

(54) FLUIDIZED COKING WITH INCREASED PRODUCTION OF LIQUIDS

(71) Applicant: ExxonMobil Research and Engineering Company, Annandale, NJ (US)

(72) Inventors: Tien V. Le, Houston, TX (US); Brenda A. Raich, Annandale, NJ (US); Bing Du, Pittstown, NJ (US); Mohsen N. Harandi, New Hope, PA (US); Suriyanarayanan Rajagopalan, Spring, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/812,396

(22) Filed: Nov. 14, 2017

(65) Prior Publication Data

US 2019/0144756 A1     May 16, 2019

(51) Int. Cl.
*C07C 2/06*     (2006.01)
*C07C 4/04*     (2006.01)
(Continued)

(52) U.S. Cl.
CPC ............... *C10B 55/10* (2013.01); *C07C 2/06* (2013.01); *C07C 4/04* (2013.01); *C07C 29/1518* (2013.01);
(Continued)

(58) Field of Classification Search
CPC ............... C10J 3/466; C10J 2300/0943; C10J 2300/0959; C10J 2300/0976;
(Continued)

(56) References Cited

U.S. PATENT DOCUMENTS 3,261,775 A    7/1966    Blaser
3,354,078 A    11/1967   Miale et al.
(Continued)

FOREIGN PATENT DOCUMENTS

EP      0372939 B1 *  9/1993  ............. C10G 25/03
WO      2013/062800 A1   5/2013

OTHER PUBLICATIONS

Database of Zeolite Structures, Structure Commission of the International Zeolite Association, Jun. 27, 2018, www.iza-structure.org/databases.

(Continued)

*Primary Examiner* — Jafar F Parsa
(74) *Attorney, Agent, or Firm* — Hsin Lin

(57) ABSTRACT

Systems and methods are provided for integrating a fluidized coking process, optionally a coke gasification process, and processes for production of additional liquid products from the coking and/or gasification process. In some aspects, the integrated processes can allow for conversion of olefins generated during a fluidized coking process to form additional liquid products. Additionally or alternately, in some aspects the integrated processes can allow for separation of syngas from the flue gas/fuel gas generated by a gasifier integrated with a fluidized coking process. This syngas can then be used to form methanol, which can then be converted in a methanol conversion process to form heavier products. In such aspects, olefins generated during the fluidized coking process can be added to the methanol conversion process to improve the yield. Additionally, in various aspects, the off-gas from the integrated conversion process can be used as an additional paraffin feed that can be recycled to one of the heat integration conduits in the fluidized coker for additional generation of olefins. This can provide a further increase in liquid yields using a carbon source ($C_{4-}$ paraf- (Continued)

fins) that is conventionally viewed as a low value product from coking.

15 Claims, 5 Drawing Sheets

(51) Int. Cl.
    *C10J 3/84* (2006.01)
    *C10B 49/22* (2006.01)
    *C10B 55/10* (2006.01)
    *C07C 29/151* (2006.01)

(52) U.S. Cl.
    CPC ............... *C10B 49/22* (2013.01); *C10J 3/84* (2013.01); *C10J 2300/0903* (2013.01); *C10J 2300/0943* (2013.01); *C10J 2300/0959* (2013.01); *C10J 2300/1659* (2013.01)

(58) Field of Classification Search
    CPC .... C10J 2300/1838; C10G 9/005; C10G 1/02; C10G 9/32; C10B 55/00; C10B 55/10
    See application file for complete search history.

(56) References Cited

U.S. PATENT DOCUMENTS

| | | | |
|---|---|---|---|
| 3,661,543 A | 5/1972 | Saxton |
| 3,702,516 A | 11/1972 | Luckenbach |
| 3,702,886 A | 11/1972 | Argauer et al. |
| 3,709,979 A | 1/1973 | Chu |
| 3,726,791 A | 4/1973 | Kimberlin et al. |
| 3,752,658 A | 8/1973 | Blaser |
| 3,759,676 A | 9/1973 | Lahn |
| 3,816,084 A | 6/1974 | Moser et al. |
| 4,016,218 A | 4/1977 | Haag et al. |
| RE29,948 E | 3/1979 | Dwyer et al. |
| 4,213,848 A | 7/1980 | Saxton |
| 4,269,696 A | 5/1981 | Metrailer |
| 4,295,956 A | 10/1981 | Metrailer |
| 4,433,185 A | 2/1984 | Tabak |
| 4,456,779 A | 6/1984 | Owen et al. |
| 4,497,968 A | 2/1985 | Wright et al. |
| 4,547,616 A | 10/1985 | Avidan et al. |
| 4,579,999 A | 4/1986 | Gould et al. |
| 4,582,815 A | 4/1986 | Bowes |
| 4,587,010 A | 5/1986 | Blaser et al. |
| 4,751,338 A | 6/1988 | Tabak et al. |
| 4,827,069 A | 5/1989 | Kushnerick et al. |
| 4,899,002 A | 2/1990 | Harandi et al. |
| 4,992,607 A | 2/1991 | Harandi et al. |
| 5,176,819 A | 1/1993 | Green |
| 5,472,596 A | 12/1995 | Kerby |
| 6,448,441 B1 | 9/2002 | Wing-Chiu et al. |
| 7,919,065 B2 | 4/2011 | Pedersen |
| 9,090,525 B2 | 7/2015 | Brown |
| 9,234,146 B2 | 1/2016 | Koseoglu |
| 2012/0006723 A1 | 1/2012 | Davis et al. |
| 2012/0055088 A1 | 3/2012 | Steele et al. |
| 2017/0233667 A1 | 8/2017 | Harandi et al. |

OTHER PUBLICATIONS

Kamienski et al., "Coking Without the Coke", Hydrocarbon Engineering, Mar. 2008.
Miale et al., "Catalysis by Crystalline Aluminosilicates", Journal of Catalysis, 1966, vol. 6, pp. 278-287.
Olson et al., "Chemical and Physical Properties of the ZSM-5 Substituional Series", Journal of Catalysis, vol. 61, 1980, pp. 390-396.
Weisz et al., "Superactive Crystalline Aluminosilicate Hydrocarbon Catalysts", Journal of Catalysis, 1965, vol. 4, pp. 527-529.
Zhao et al., "Coal to Clean Gasoline", Hydrocarbon Engineering, Mar. 2008.
The International Search Report and Written Opinion of PCT/US2018/059523 dated Apr. 24, 2019.
The International Search Report and Written Opinion of PCT/US2018/059527 dated Apr. 24, 2019.

* cited by examiner

FLUIDIZED COKING WITH INCREASED PRODUCTION OF LIQUIDS

CROSS-REFERENCE TO RELATED APPLICATIONS

This application is related to one other co-pending U.S. application, filed on even date herewith, and identified by the following 15/812,340 entitled "Gasification with Enriched Oxygen for Production of Synthesis Gas". This co-pending U.S. application is hereby incorporated by reference in its entirety.

FIELD

Systems and methods are provided for integration of fluidized coking with processes for generation of additional liquid products from overhead gas streams.

BACKGROUND

Coking is a carbon rejection process that is commonly used for upgrading of heavy oil feeds and/or feeds that are challenging to process, such as feeds with a low ratio of hydrogen to carbon. In addition to producing a variety of liquid products, typical coking processes can also generate a substantial amount of coke. Because the coke contains carbon, the coke is potentially a source of additional valuable products in a refinery setting. However, fully realizing this potential remains an ongoing challenge.

Coking processes in modern refinery settings can typically be categorized as delayed coking or fluidized bed coking. Fluidized bed coking is a petroleum refining process in which heavy petroleum feeds, typically the non-distillable residues (resids) from the fractionation of heavy oils are converted to lighter, more useful products by thermal decomposition (coking) at elevated reaction temperatures, typically 480° C. to 590° C., (~900° F. to 1100° F.) and in most cases from 500° C. to 550° C. (~930° F. to 1020° F.). Heavy oils which may be processed by the fluid coking process include heavy atmospheric resids, petroleum vacuum distillation bottoms, aromatic extracts, asphalts, and bitumens from tar sands, tar pits and pitch lakes of Canada (Athabasca, Alta.), Trinidad, Southern California (La Brea (Los Angeles), McKittrick (Bakersfield, Calif.), Carpinteria (Santa Barbara County, Calif.), Lake Bermudez (Venezuela) and similar deposits such as those found in Texas, Peru, Iran, Russia and Poland.

Fluidized coking is carried out in a unit with a large reactor containing hot coke particles which are maintained in the fluidized condition at the required reaction temperature with steam injected at the bottom of the vessel with the average direction of movement of the coke particles being downwards through the bed. The heavy oil feed is heated to a pumpable temperature, typically in the range of 350° C. to 400° C. (~660° F. to 750° F.), mixed with atomizing steam, and fed through multiple feed nozzles arranged at several successive levels in the reactor. Steam is injected into a stripping section at the bottom of the reactor and passes upwards through the coke particles descending through the dense phase of the fluid bed in the main part of the reactor above the stripping section. Part of the feed liquid coats the coke particles in the fluidized bed and is subsequently cracked into layers of solid coke and lighter products which evolve as gas or vaporized liquid. Reactor pressure is relatively low in order to favor vaporization of the hydrocarbon vapors which pass upwards from dense phase into dilute phase of the fluid bed in the coking zone and into cyclones at the top of the coking zone where most of the entrained solids are separated from the gas phase by centrifugal force in one or more cyclones and returned to the dense fluidized bed by gravity through the cyclone diplegs. The mixture of steam and hydrocarbon vapors from the reactor is subsequently discharged from the cyclone gas outlets into a scrubber section in a plenum located above the coking zone and separated from it by a partition. It is quenched in the scrubber section by contact with liquid descending over sheds, A pumparound loop circulates condensed liquid to an external cooler and back to the top shed row of the scrubber section to provide cooling for the quench and condensation of the heaviest fraction of the liquid product. This heavy fraction is typically recycled to extinction by feeding back to the coking zone in the reactor.

The coke particles formed in the coking zone pass downwards in the reactor and leave the bottom of the reactor vessel through a stripper section where they are exposed to steam in order to remove occluded hydrocarbons. The solid coke from the reactor, consisting mainly of carbon with lesser amounts of hydrogen, sulfur, nitrogen, and traces of vanadium, nickel, iron, and other elements derived from the feed, passes through the stripper and out of the reactor vessel to a burner or heater where it is partly burned in a fluidized bed with air to raise its temperature from 480° C. to 700° C. (~900° F. to 1300° F.) to supply the heat required for the endothermic coking reactions, after which a portion of the hot coke particles is recirculated to the fluidized bed reaction zone to transfer the heat to the reactor and to act as nuclei for the coke formation. The balance is withdrawn as coke product. The net coke yield is only about 65 percent of that produced by delayed coking.

The Flexicoking™ process, developed by Exxon Research and Engineering Company, is a variant of the fluid coking process that is operated in a unit including a reactor and a heater, but also including a gasifier for gasifying the coke product by reaction with an air/steam mixture to form a low heating value fuel gas. A stream of coke passes from the heater to the gasifier where all but a small fraction of the coke is gasified to a low-BTU gas (~120 BTU/standard cubic feet) by the addition of steam and air in a fluidized bed in an oxygen-deficient environment to form fuel gas comprising carbon monoxide and hydrogen. In a conventional Flexicoking™ configuration, the fuel gas product from the gasifier, containing entrained coke particles, is returned to the heater to provide most of the heat required for thermal cracking in the reactor with the balance of the reactor heat requirement supplied by combustion in the heater. A small amount of net coke (about 1 percent of feed) is withdrawn from the heater to purge the system of metals and ash. The liquid yield and properties are comparable to those from fluid coking. The fuel gas product is withdrawn from the heater following separation in internal cyclones which return coke particles through their diplegs.

The Flexicoking process is described in patents of Exxon Research and Engineering Company, including, for example, U.S. Pat. No. 3,661,543 (Saxton), U.S. Pat. No. 3,759,676 (Lahn), U.S. Pat. No. 3,816,084 (Moser), U.S. Pat. No. 3,702,516 (Luckenbach), U.S. Pat. No. 4,269,696 (Metrailer). A variant is described in U.S. Pat. No. 4,213,848 (Saxton) in which the heat requirement of the reactor coking zone is satisfied by introducing a stream of light hydrocarbons from the product fractionator into the reactor instead of the stream of hot coke particles from the heater. Another variant is described in U.S. Pat. No. 5,472,596 (Kerby) using a stream of light paraffins injected into the hot coke return line to generate olefins. Early work proposed units with a stacked configuration but later units have migrated to a side-by-side arrangement.

Although the fuel gas from the gasifier can be used for heating, due to the low energy content, burning of the fuel gas for heat can still represent a relatively low value use for the carbon in the fuel gas. Similarly, the flue gas generated from the burner of a fluidized coking process has traditionally been viewed as a low value product. Additionally, the primary product stream derived from fluidized coking (including Flexicoking™) typically includes gases that are formed during the coking process. After separation of liquid products formed during coking, the remaining gases represent yet another product that is traditionally viewed as a low value product. What is needed are systems and methods that can allow for generation of still higher economic value products from the various gas products generated during fluidized coking type processes.

U.S. Pat. Nos. 9,090,525 and 4,899,002 describes system and methods for converting methanol to light olefins and/or conversion of methanol to gasoline boiling range compounds, and optionally distillate boiling range compounds via an olefinic intermediate.

SUMMARY

In various aspects, methods for performing fluidized coking on a feed are provided. The methods can include exposing a feedstock comprising a T10 distillation point of 343° C. or more to a fluidized bed comprising solid particles in a reactor under coking conditions to form a coker effluent. The solid particles can optionally correspond to coke particles. The thermal cracking conditions can be effective for depositing coke on the solid particles. Optionally, the thermal cracking conditions can be effective for conversion of 10 wt % or more of the feedstock relative to 343° C. An oxygen-containing stream and steam can be introduced into a coke combustion stage. At least a portion of the solid particles comprising deposited coke can be passed from the reactor to the coke combustion stage. Optionally, the coke combustion stage can correspond to a gasification stage, such as a gasifier. The solid particles comprising deposited coke can be exposed to combustion and/or gasification conditions to form a gas phase product comprising $H_2$, CO, $CO_2$, and/or $H_2S$, and partially combusted and/or gasified solid particles. A first portion of the partially combusted and/or gasified solid particles from the coke combustion and/or gasification stage can be removed, while a second portion of the partially combusted and/or gasified solid particles can be passed from the coke combustion stage (such as a gasifier) to the reactor. The coker effluent can be separated to form a lower boiling product comprising $C_2$-$C_4$ olefins and a higher boiling product comprising a 343° C.– portion.

In some aspects, at least a portion of the lower boiling product can be exposed to a catalyst under olefin oligomerization conditions to form an oligomerized product and a light ends product comprising $C_2$-$C_4$ paraffins. At least a portion of the light ends product can be introduced into the second portion of the partially combusted and/or gasified solid particles after the second portion of the partially combusted solid particles exits from the coke combustion stage (such as a gasifier), and preferably prior to passing the second portion of the partially combusted and/or gasified solid particles into the reactor. The light ends product can be exposed to the partially combusted and/or gasified solid particles at a suitable temperature for conversion of paraffins to olefins, such as 500° C. to 750° C., or 600° C. to 700° C.

In some aspects, $CO_2$, $H_2S$, or a combination thereof can be separated from the gas phase product to form at least a synthesis gas stream. Optionally, the synthesis gas stream can correspond to 80 vol % or more of $H_2$ and CO. At least a portion of the synthesis gas stream can be exposed to a methanol synthesis catalyst under synthesis conditions to form a methanol-containing product stream. At least a portion of the methanol-containing product stream can then be exposed to a conversion catalyst under conversion conditions to form a conversion product comprising $C_{5+}$ hydrocarbons and a light ends product comprising $C_2$-$C_4$ paraffins. At least a portion of the light ends product can be introduced into the second portion of the partially combusted and/or gasified solid particles after the second portion of the partially combusted solid particles exits from the coke combustion stage (such as a gasifier), and preferably prior to passing the second portion of the partially combusted and/or gasified solid particles into the reactor. The light ends product can be exposed to the partially combusted and/or gasified solid particles at a suitable temperature for conversion of paraffins to olefins, such as 500° C. to 750° C., or 600° C. to 700° C. In such aspects, the method can optionally further include separating the coker effluent to form a lower boiling product comprising $C_2$-$C_4$ olefins and a higher boiling product comprising a 343° C.– portion. At least a portion of the lower boiling product can be exposed (in combination with the methanol-containing product stream) to the conversion catalyst under the conversion conditions.

Optionally, an additional paraffin-containing stream can be introduced into the second portion of the partially combusted and/or gasified solid particles after the second portion of the partially combusted and/or gasified solid particles exits from the gasifier, and preferably prior to passing the second portion of the partially combusted and/or gasified solid particles into the reactor. The additional paraffin-containing stream can also be exposed to the partially combusted and/or gasified solid particles at a suitable temperature for conversion of paraffins to olefins.

In some aspects, passing solid particles comprising deposited coke from the reactor to the gasifier can correspond to passing solid particles comprising deposited coke to a heater, and then passing solid particles comprising deposited coke from the heater to the gasifier. In some aspects, passing partially gasified solid particles from the gasifier to the reactor can correspond to passing partially gasified solid particles to a coking section of the reactor, to a stripping section of the reactor, or a combination thereof.

In some aspects, the fluidized coking process can correspond to a process that reduces or minimizes formation of deposits in an associated gasifier. In such aspects, exposing solid particles comprising deposited coke to gasification conditions can result in deposition of less than 0.1 wt % of metal oxides on a wall of the gasifier, relative to a metals content of the feedstock.

In various aspects, an integrated fluidized coking system is also provided. The system can include a fluidized bed coker comprising a coker feed inlet, a cold coke outlet, at least one hot coke inlet, and a coker product outlet. The system can further include a coke combustion reactor, such as a gasifier, comprising: a coke combustion and/or gasifier inlet in fluid communication with the cold coke outlet, a coke combustion and/or gasifier outlet in fluid communication with the at least one hot coke inlet via at least one hot coke conduit, at least one coke combustion and/or gasifier gas inlet, and a fuel gas outlet.

In some aspects, the system can further include a first separation stage comprising a first separation stage inlet in fluid communication with the coker product outlet, a first separation stage heavy product outlet and a first separation stage light ends outlet. In such aspects, the system can also further include an oligomerization reactor comprising an oligomerization inlet in fluid communication with the first separation stage light ends outlet, an oligomerized product outlet, and an oligomerization light ends outlet in fluid communication with the at least one hot coke conduit. Optionally the coke combustion reactor can correspond to a gasifier, with the at least one coke combustion gas inlet comprising at least one gasifier gas inlet.

In some aspects, the system can further include a $CO_2$ separation stage comprising a separation stage inlet in fluid communication with the fuel gas outlet, a separation stage outlet in fluid communication with at least one gasifier input gas inlet, and a synthesis gas outlet. In such aspects, the system can further include a methanol synthesis reactor comprising a synthesis gas inlet in fluid communication with the synthesis gas outlet and a methanol product outlet. In such aspects, the system can optionally further include a methanol conversion stage comprising a conversion inlet in fluid communication with the methanol product outlet, a conversion stage heavy product outlet, and a conversion stage light ends outlet in fluid communication with the at least one hot coke conduit. Optionally, the system can further include a first separation stage, the first separation stage comprising a first separation stage inlet in fluid communication with the coker product outlet, a first separation stage heavy product outlet and a first separation stage light ends outlet in fluid communication with the conversion inlet.

In some aspects, the system can further include a heater, the gasifier coke inlet being in indirect fluid communication with the cold coke outlet via the heater, the gasifier coke outlet being in indirect fluid communication with the at least one hot coke inlet via the heater.

In some aspects, the at least one hot coke inlet can be in fluid communication with a coking section of the reactor, a stripping section of the reactor, or a combination thereof.

DETAILED DESCRIPTION

Figure 1:
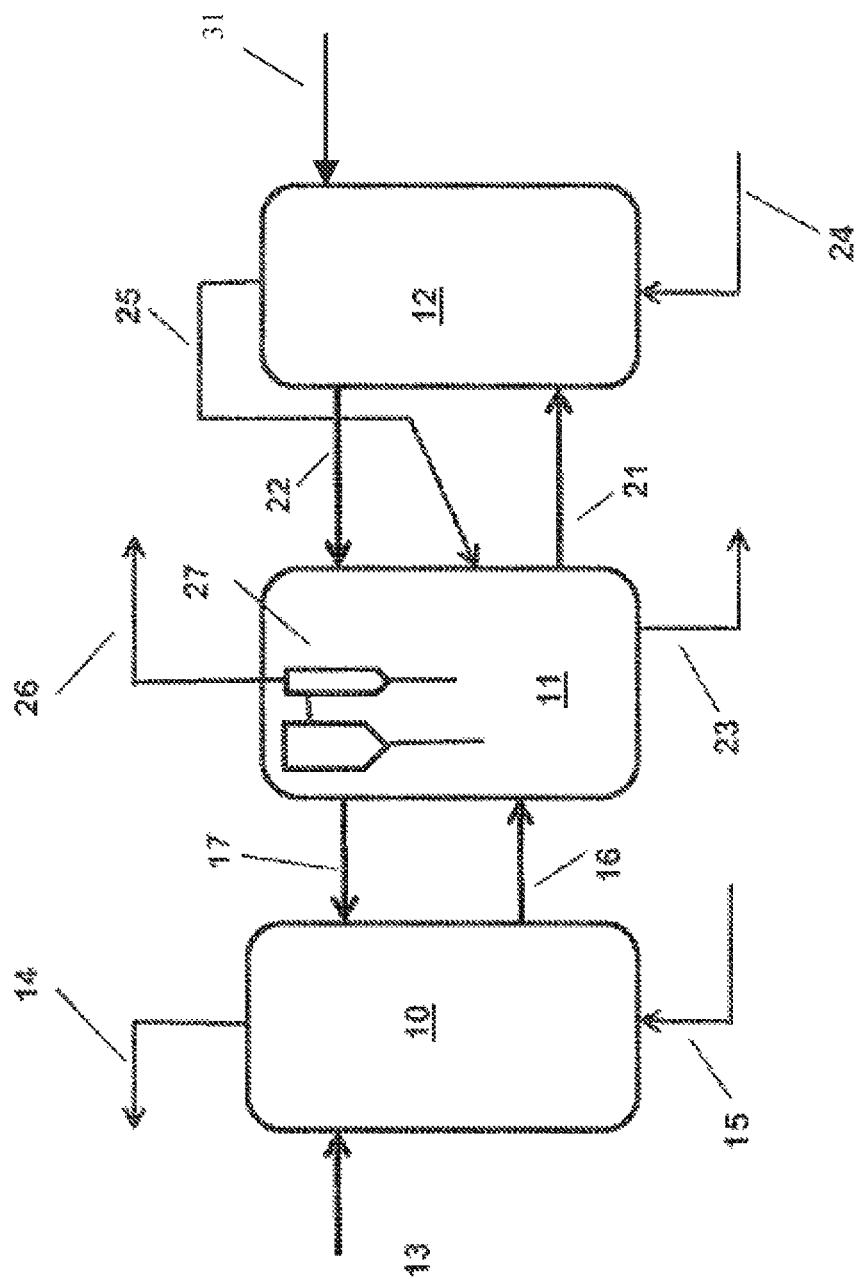
FIG. 1 shows an example of a fluidized bed coking system including a coker, a heater, and a gasifier.

All numerical values within the detailed description and the claims herein are modified by "about" or "approximately" the indicated value, and take into account experimental error and variations that would be expected by a person having ordinary skill in the art.

In this discussion, some feeds, fractions, or products may be described based on a fraction that boils below or above a specified distillation point. For example, a 343° C.− product corresponds to a product that contains components with a boiling point (at standard temperature and pressure) of 343° C. or less. Similarly, a 343° C.+ product corresponds to a product that contains components with a boiling point of 343° C. or more.

Overview

In various aspects, systems and methods are provided for integrating a fluidized coking process, optionally a coke gasification process, and processes for production of additional liquid products from the coking and/or gasification process. In some aspects, the integrated processes can allow for conversion of olefins generated during a fluidized coking process to form additional liquid products. Additionally or alternately, in some aspects the integrated processes can allow for separation of syngas from the flue gas/fuel gas generated by a gasifier integrated with a fluidized coking process. This syngas can then be used to form methanol, which can then be converted in a methanol conversion process to form heavier products. In such aspects, olefins generated during the fluidized coking process can be added to the methanol conversion process to improve the yield. Additionally, in various aspects, the off-gas from the integrated conversion process can be used as an additional paraffin feed that can be recycled to one of the heat integration conduits in the fluidized coker for additional generation of olefins. This can provide a further increase in liquid yields using a carbon source ($C_{4-}$ paraffins) that is conventionally viewed as a low value product from coking.

The hydrocarbon vapors generated as the primary product of a fluidized coking process can include both fuels boiling range products ($C_{5+}$) and light ends ($C_{4-}$). Conventionally, a fractionator or another type of separation stage can be used to separate the fuels boiling range products into various desired product fractions, such as coker naphtha and coker distillate fractions. The light ends are conventionally viewed as a low value product suitable (at best) for uses such as fuel gas in the refinery. However, because of the conditions present in a coking environment, a portion of the light ends formed during fluidized coking can correspond to olefins. The amount of olefins in the light ends can correspond to 4 wt % to 5 wt % relative to the weight of fresh feed to the coking process, while the amount of paraffins can correspond to roughly another 5 wt % relative to the weight of the fresh feed. These olefins can provide an opportunity for formation of additional liquid products. Additionally, based on the elevated temperatures present in certain conduits of an integrated processing environment that includes a fluidized coker, the $C_{2+}$ paraffins in the light ends can potentially be converted to additional olefins to form still more liquid products. In particular, the hot coke (or other solid particle) return lines in a fluidized coker environment can allow for conversion of paraffins to olefins within the return conduit. Converting paraffins to olefins can allow for recycle of additional light ends back to the oligomerization reactor for liquid formation, thus substantially reducing or minimizing the amount of carbon that is lost to low value uses from the non-coke products of the coking process. For example, performing olefin oligomerization and recycling paraffins to form additional olefins can increase the net liquid product ($C_{5+}$) yield from coking by 3 wt % to 8 wt % relative to the weight of the fresh feed to the coking process. It is noted that a typical fluidized coking process can involve recycle of at least a portion of the coker effluent, so that the feed to a fluidized coking process can correspond to a combination of fresh feed and recycled feed.

In some aspects, the light ends separated from the coker effluent of a fluidized coker can be used as an input feed for an olefin oligomerization process to form naphtha boiling range (or possibly higher boiling range) compounds from the $C_2$, $C_3$, and/or $C_4$ olefins present in the light ends. Because the feed stream to the oligomerization process corresponds to light ends, any sulfur present in the feed will typically correspond to $H_2S$, which can be easily separated from the resulting oligomerized products. As a result, the additional liquids formed from the oligomerization can substantially correspond to a naphtha boiling range product (or possibly a higher boiling range product) with a reduced or minimized sulfur content. Any hydrocarbons not oligomerized into liquid products can be recycled for exposure to conditions suitable for conversion of paraffins to olefins.

Table 1 shows an example of the ability to convert paraffins to olefins within a conduit in a fluidized coking environment. For the data in Table 1, an isobutane feed was exposed to coke particles from a gasifier at a total pressure of 45 psi-a (~310 kPa-a) and an isobutane partial pressure of 32 psi-a (~220 kPa). The feed was exposed to the coke particles at 640° C. for a residence time of 2.6 seconds at a catalyst to feed weight ratio of 0.1. Under these conditions, roughly 28 wt % of the isobutane was converted. Of this converted isobutane, more than 50% was converted to isobutenes while another 25% was converted to propene, indicating a good yield of olefins relative to the amount of conversion. It is noted that the total weight of products generated is greater than the original feed weight, due to incorporation of some additional oxygen into the resulting products.

TABLE 1

Conversion of Isobutane in the Presence of Heated Coke (640° C.)

| Conversion Product | Yield (wt %) |
|---|---|
| COx | 2.9 |
| H2 | 0.4 |
| Methane | 2.8 |
| C2- (dry gas) | 6.2 |
| Propene | 7.0 |
| Isobutene | 14.3 |
| n-butenes | 0.1 |
| Isobutane | 72.5 |

Although the conversion of paraffins to olefins is roughly 25 wt %, any unconverted paraffins can be recycled again for multiple passes. Some purging can typically be necessary to avoid buildup of methane, but this can still allow for conversion of a substantial portion of the $C_2$-$C_4$ paraffins generated during coking into olefins for eventual incorporation into a liquid ($C_{5+}$) product. In various aspects, conversion of paraffins to olefins can be performed in a conduit for transfer of gas phase products from a heater and/or gasifier to another vessel. The temperature in the conduit can be 500° C. to 750° C., or 600° C. to 700° C.

Optionally, if additional refinery fuel gas, natural gas liquids, and/or other streams containing light paraffins are available, such additional paraffin-containing streams can be introduced into the fluidized coking system to allow still further generation of olefins. Because multiple passes can be performed to allow for substantially complete conversion of paraffins to olefins, introduction of one or more streams containing additional paraffins can provide a further increase in olefin yield and/or subsequent product yield. It is noted that adding further paraffins to the integrated coking and gasification system may require additional burning of coke in the fluidized coker to maintain heat balance. However, this can typically correspond to only a modest change in the relative amount of coke that is burned as fuel versus gasified to form additional gasification products.

In addition to providing additional yield a low sulfur fuel or fuel blending product, forming additional liquids from the light ends portion of a coker effluent can potentially provide other advantages. For example, a heavy feed can be upgraded to form olefins and/or additional liquid products without requiring an additional cracking unit, such as a fluidized catalytic cracking unit. The integrated process can upgrade the olefins from the coker effluent with little or no additional feed preparation, other than to separate the light ends from portions of the coker effluent that already correspond to liquid products. The recycle of unreacted hydrocarbons can also assist with fluidization in conduits for return of particles from a burner or gasifier back to the reactor. This can reduce the amount of additional steam required for fluidization.

Additionally or alternately, for fluidized coking processes that include an integrated gasifier, additional liquid products can be formed from the gasifier flue gas or fuel gas. One of the difficulties with using petroleum coke, coal, and/or heavy oils as a feed for gasification is that such feeds can potentially contain a relatively high percentage of transition metals, such as iron, nickel, and vanadium. During conventional operation of a gasifier, these transition metals are converted into a "slag" that tends to be corrosive for the internal structures of the gasifier. As a result, gasifiers can typically have relatively short operating lengths between shutdown events, such as operating lengths of roughly 3 months to 18 months.

For an independently operated gasifier, frequent shutdown events may be acceptable. However, for a gasifier that is integrated to provide heat balance to another process, such as a fluidized bed coker, a short cycle length for the gasifier can force a short cycle length for the coker as well. In order to overcome this problem, a gasifier that is thermally integrated with a fluidized bed coking process, such as a Flexicoking™ process, can be operated under conditions that reduce, minimize, or eliminate formation of slag. Typically this can be achieved by using air as at least a portion of the oxygen source for the gasifier that is integrated with the fluidized bed coking process. The additional nitrogen in air can provide a diluent for the gasifier environment that can reduce or minimize slag formation. Instead of forming a slag or other glassy type product containing metals, the metals in the coke can be retained in coke form and purged from the integrated system. This can allow the removal or disposition of the metals to be performed in a secondary device or location. By avoiding formation of the corrosive slag, the cycle length of the integrated coker and gasifier can be substantially improved.

One difficulty with operating an integrated coker and gasifier to avoid slag formation is that the resulting fuel gas generated in the gasifier can have a relatively low BTU value. Because of the substantial amount of nitrogen introduced into the gasifier along with the oxygen, the nitrogen content of the fuel gas generated from an integrated fluidized bed/gasifier system can be up to 55 vol %. This can present a variety of problems when attempting to find a high value use for the carbon in the fuel gas. For example, this low BTU gas includes a sufficient amount of diluent (such as nitrogen) that it is not directly suitable as a fuel in various types of burners in a refinery setting. Instead, use of the fuel gas as a fuel may require distribution of the fuel gas across multiple burners, so that the fuel gas can be blended with other fuels having a higher energy density. Another difficulty is that the low BTU gas is also a low pressure stream when it emerges from the gasifier. Attempting to compress the fuel gas to match pressures in another processing environment would require compressing the nitrogen in the fuel gas, meaning a substantial additional compression cost with little value in return.

In various aspects, instead of using the low BTU fuel gas as a fuel, the low BTU fuel gas can undergo one or more separations to form synthesis gas stream. The synthesis gas can then be used for methanol production. The resulting methanol can then be converted into heavier products. To further improve the yields from methanol conversion, the light ends stream separated from the primary coking product can be added to the methanol conversion process. The olefins from the light ends can be incorporated into the methanol conversion process. The paraffins from the light ends are not reactive, but can again be recycled for formation of further olefins. This can allow for production of substantial additional liquid product from the integrated coking process, such as 10 wt % to 25 wt % of additional liquid product ($C_{5+}$) relative to a weight of the feed to the coking process.

In this discussion and the claims below, a zeolite is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", $6^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework.

Fluidized Coking with Integrated Gasification

In this description, the term "Flexicoking" (trademark of ExxonMobil Research and Engineering Company) is used to designate a fluid coking process in which heavy petroleum feeds are subjected to thermal cracking in a fluidized bed of heated solid particles to produce hydrocarbons of lower molecular weight and boiling point along with coke as a by-product which is deposited on the solid particles in the fluidized bed. The resulting coke can then converted to a fuel gas by contact at elevated temperature with steam and an oxygen-containing gas in a gasification reactor (gasifier). This type of configuration can more generally be referred to as an integration of fluidized bed coking with gasification.

It is noted that in some alternative aspects, olefin oligomerization processes as described herein may be suitable for use with fluidized coking reactors that are integrated with a conventional burner as opposed to a gasifier or gasifier/heater combination. In this discussion, the term coke combustion stage can generally be used to refer to both burners for conventional fluidized coking systems and the gasifiers or gasifier/heater combinations for Flexicoking™ systems and other fluidized coking systems with an integrated gasifier.

In various aspects, an integrated fluidized bed coker and gasifier, optionally also including a heater, can be used to process a feed by first coking the feed and then gasifying the resulting coke. This can generate a fuel gas product, withdrawn from the gasifier or the optional heater, that can then be further processed to increase the concentration of synthesis gas in the product. The product with increased synthesis gas concentration can then be used as an input for production of methanol, optionally after further processing to adjust the $H_2$ to CO ratio in the synthesis gas.

FIG. 1 shows an example of a Flexicoker unit (i.e., a system including a gasifier that is thermally integrated with a fluidized bed coker) with three reaction vessels: reactor, heater and gasifier. The unit comprises reactor section 10 with the coking zone and its associated stripping and scrubbing sections (not separately indicated), heater section 11 and gasifier section 12. The relationship of the coking zone, scrubbing zone and stripping zone in the reactor section is shown, for example, in U.S. Pat. No. 5,472,596, to which reference is made for a description of the Flexicoking unit and its reactor section. A heavy oil feed is introduced into the unit by line 13 and cracked hydrocarbon product withdrawn through line 14. Fluidizing and stripping steam is supplied by line 15. Cold coke is taken out from the stripping section at the base of reactor 10 by means of line 16 and passed to heater 11. The term "cold" as applied to the temperature of the withdrawn coke is, of course, decidedly relative since it is well above ambient at the operating temperature of the stripping section. Hot coke is circulated from heater 11 to reactor 10 through line 17. Coke from heater 11 is transferred to gasifier 12 through line 21 and hot, partly gasified particles of coke are circulated from the gasifier back to the heater through line 22. The excess coke is withdrawn from the heater 11 by way of line 23. In conventional configurations, gasifier 12 is provided with its supply of steam and air by line 24 and hot fuel gas is taken from the gasifier to the heater though line 25. In some alternative aspects, instead of supplying air via a line 24 to the gasifier 12, a stream of oxygen with 95 vol % purity or more can be provided, such as an oxygen stream from an air separation unit. In such aspects, in addition to supplying a stream of oxygen, a stream of an additional diluent gas can be supplied by line 31. The additional diluent gas can correspond to, for example, $CO_2$ separated from the fuel gas generated during the gasification. The fuel gas is taken out from the unit through line 26 on the heater; coke fines are removed from the fuel gas in heater cyclone system 27 comprising serially connected primary and secondary cyclones with diplegs which return the separated fines to the fluid bed in the heater. The fuel gas from line 26 can then undergo further processing. For example, in some aspects, the fuel gas from line 26 can be passed into a separation stage for separation of $CO_2$ (and/or $H_2S$). This can result in a stream with an increased concentration of synthesis gas, which can then be passed into a conversion stage for conversion of synthesis gas to methanol.

It is noted that in some optional aspects, heater cyclone system 27 can be located in a separate vessel (not shown) rather than in heater 11. In such aspects, line 26 can withdraw the fuel gas from the separate vessel, and the line 23 for purging excess coke can correspond to a line transporting coke fines away from the separate vessel. These coke fines and/or other partially gasified coke particles that are vented from the heater (or the gasifier) can have an increased content of metals relative to the feedstock. For example, the weight percentage of metals in the coke particles vented from the system (relative to the weight of the vented particles) can be greater than the weight percent of metals in the feedstock (relative to the weight of the feedstock). In other words, the metals from the feedstock are concentrated in the vented coke particles. Since the gasifier conditions avoid the creation of slag, the vented coke particles correspond to the mechanism for removal of metals from the coker/gasifier environment. In some aspects, the metals can correspond to a combination of nickel, vanadium, and/or iron. Additionally or alternately, the gasifier conditions can cause substantially no deposition of metal oxides on the interior walls of the gasifier, such as deposition of less than 0.1 wt % of the metals present in the feedstock introduced into the coker/gasifier system, or less than 0.01 wt %.

In configurations such as FIG. 1, the system elements shown in the figure can be characterized based on fluid communication between the elements. For example, reactor section 10 is in direct fluid communication with heater 11. Reactor section 10 is also in indirect fluid communication with gasifier 12 via heater 11.

As an alternative, integration of a fluidized bed coker with a gasifier can also be accomplished without the use of an intermediate heater. In such alternative aspects, the cold coke from the reactor can be transferred directly to the gasifier. This transfer, in almost all cases, will be unequivocally direct with one end of the tubular transfer line connected to the coke outlet of the reactor and its other end connected to the coke inlet of the gasifier with no intervening reaction vessel, i.e. heater. The presence of devices other than the heater is not however to be excluded, e.g. inlets for lift gas etc. Similarly, while the hot, partly gasified coke particles from the gasifier are returned directly from the gasifier to the reactor this signifies only that there is to be no intervening heater as in the conventional three-vessel Flexicoker™ but that other devices may be present between the gasifier and the reactor, e.g. gas lift inlets and outlets.

Figure 2:
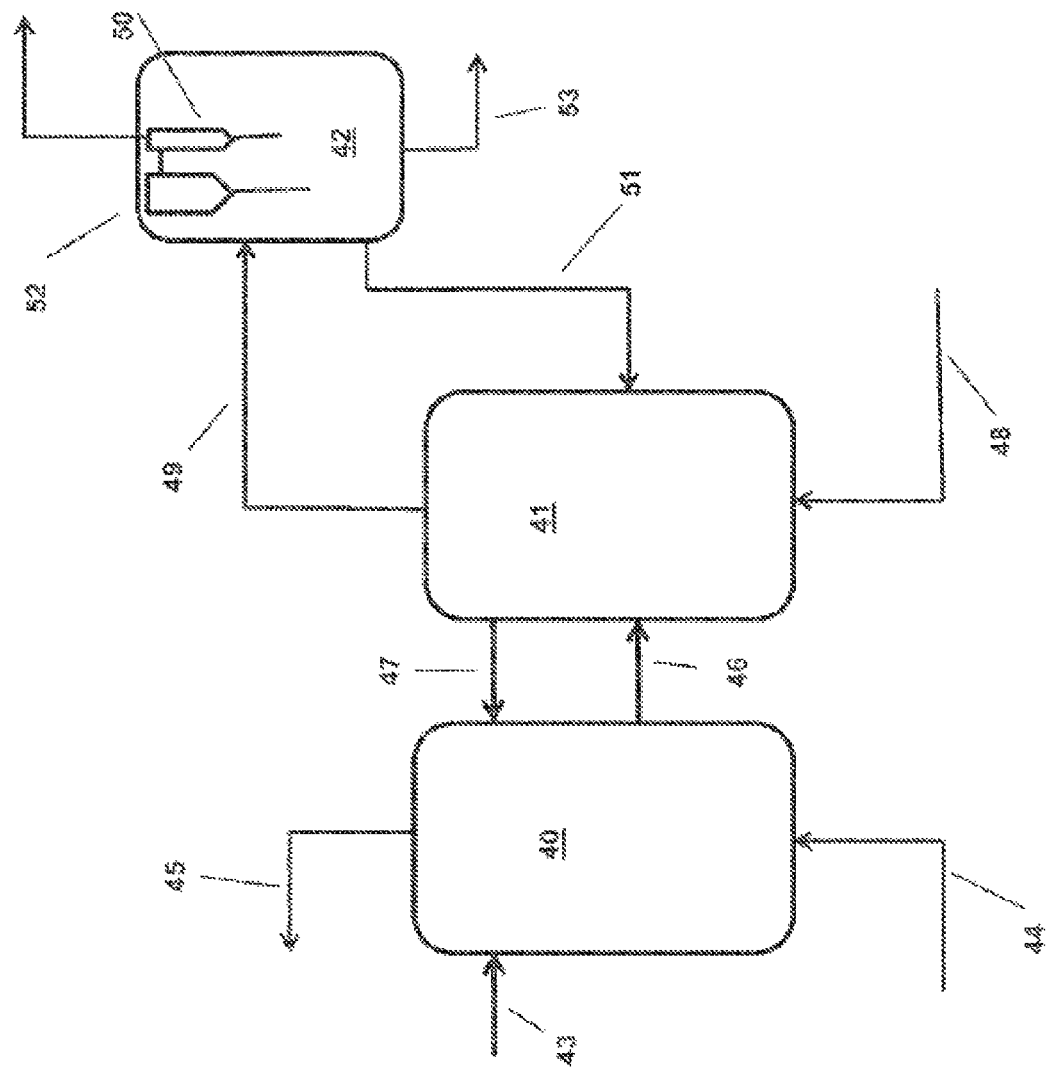
FIG. 2 shows an example of a fluidized bed coking system including a coker and a gasifier.

FIG. 2 shows an example of integration of a fluidized bed coker with a gasifier but without a separate heater vessel. In the configuration shown in FIG. 2, the cyclones for separating fuel gas from catalyst fines are located in a separate vessel. In other aspects, the cyclones can be included in gasifier vessel 41.

In the configuration shown in FIG. 2, the configuration includes a reactor 40, a main gasifier vessel 41 and a separator 42. The heavy oil feed is introduced into reactor 40 through line 43 and fluidizing/stripping gas through line 44; cracked hydrocarbon products are taken out through line 45. Cold, stripped coke is routed directly from reactor 40 to gasifier 41 by way of line 46 and hot coke returned to the reactor in line 47. Steam and oxygen are supplied through line 48. The flow of gas containing coke fines is routed to separator vessel 42 through line 49 which is connected to a gas outlet of the main gasifier vessel 41. The fines are separated from the gas flow in cyclone system 50 comprising serially connected primary and secondary cyclones with diplegs which return the separated fines to the separator vessel. The separated fines are then returned to the main gasifier vessel through return line 51 and the fuel gas product taken out by way of line 52. Coke is purged from the separator through line 53. The fuel gas from line 52 can then undergo further processing for separation of $CO_2$ (and/or $H_2S$) and conversion of synthesis gas to methanol.

The coker and gasifier can be operated according to the parameters necessary for the required coking processes. Thus, the heavy oil feed will typically be a heavy (high boiling) reduced petroleum crude; petroleum atmospheric distillation bottoms; petroleum vacuum distillation bottoms, or residuum; pitch; asphalt; bitumen; other heavy hydrocarbon residues; tar sand oil; shale oil; or even a coal slurry or coal liquefaction product such as coal liquefaction bottoms. Such feeds will typically have a Conradson Carbon Residue (ASTM D189-165) of at least 5 wt. %, generally from 5 to 50 wt. %. Preferably, the feed is a petroleum vacuum residuum.

A typical petroleum chargestock suitable for processing in a fluidized bed coker can have a composition and properties within the ranges set forth below in Table 2.

TABLE 2

| Example of Coker Feedstock | | |
|---|---|---|
| Conradson Carbon | 5 to 40 | wt. % |
| API Gravity | −10 to 35° | |
| Boiling Point | 340° C.+ to 650° C.+ | |
| Sulfur | 1.5 to 8 | wt. % |
| Hydrogen | 9 to 11 | wt. % |
| Nitrogen | 0.2 to 2 | wt. % |
| Carbon | 80 to 86 | wt. % |
| Metals | 1 to 2000 | wppm |

More generally, the feed to the fluidized bed coker can have a T10 distillation point of 343° C. or more, or 371° C. or more.

The heavy oil feed, pre-heated to a temperature at which it is flowable and pumpable, is introduced into the coking reactor towards the top of the reactor vessel through injection nozzles which are constructed to produce a spray of the feed into the bed of fluidized coke particles in the vessel. Temperatures in the coking zone of the reactor are typically in the range of 450° C. to 850° C. and pressures are kept at a relatively low level, typically in the range of 120 kPag to 400 kPag (~17 psig to 58 psig), and most usually from 200 kPag to 350 kPag (~29 psig to 51 psig), in order to facilitate fast drying of the coke particles, preventing the formation of sticky, adherent high molecular weight hydrocarbon deposits on the particles which could lead to reactor fouling. The conditions can be selected so that a desired amount of conversion of the feedstock occurs in the fluidized bed reactor. For example, the conditions can be selected to achieve at least 10 wt % conversion relative to 343° C. (or 371° C.), or at least 20 wt % conversion relative 343° C. (or 371° C.), or at least 40 wt % conversion relative to 343° C. (or 371° C.), such as up to 80 wt % conversion or possibly still higher. The light hydrocarbon products of the coking (thermal cracking) reactions vaporize, mix with the fluidizing steam and pass upwardly through the dense phase of the fluidized bed into a dilute phase zone above the dense fluidized bed of coke particles. This mixture of vaporized hydrocarbon products formed in the coking reactions flows upwardly through the dilute phase with the steam at superficial velocities of roughly 1 to 2 meters per second (~3 to 6 feet per second), entraining some fine solid particles of coke which are separated from the cracking vapors in the reactor cyclones as described above. The cracked hydrocarbon vapors pass out of the cyclones into the scrubbing section of the reactor and then to product fractionation and recovery.

In this discussion, reference may be made to conversion of a feedstock relative to a conversion temperature. Conversion relative to a temperature can be defined based on the portion of the feedstock that boils at greater than the conversion temperature. The amount of conversion during a process (or optionally across multiple processes) can correspond to the weight percentage of the feedstock converted from boiling above the conversion temperature to boiling below the conversion temperature. As an illustrative hypothetical example, consider a feedstock that includes 40 wt % of components that boil at 650° F. (~343° C.) or greater. By definition, the remaining 60 wt % of the feedstock boils at less than 650° F. (~343° C.). For such a feedstock, the amount of conversion relative to a conversion temperature of ~343° C. would be based only on the 40 wt % that initially boils at ~343° C. or greater. If such a feedstock could be exposed to a process with 30% conversion relative to a ~343° C. conversion temperature, the resulting product would include 72 wt % of ~343° C.− components and 28 wt % of ~343° C.+ components.

As the cracking process proceeds in the reactor, the coke particles pass downwardly through the coking zone, through the stripping zone, where occluded hydrocarbons are stripped off by the ascending current of fluidizing gas (steam). They then exit the coking reactor and pass to the gasification reactor (gasifier) which contains a fluidized bed of solid particles and which operates at a temperature higher than that of the reactor coking zone. In the gasifier, the coke particles are converted by reaction at the elevated temperature with steam and an oxygen-containing gas into a fuel gas comprising carbon monoxide and hydrogen.

The gasification zone is typically maintained at a high temperature ranging from 850° C. to 1000° C. (~1560° F. to 1830° F.) and a pressure ranging from 0 kPag to 1000 kPag (~0 psig to 150 psig), preferably from 200 kPag to 400 kPag (~30 psig to 60 psig). Steam and an oxygen-containing gas are introduced to provide fluidization and an oxygen source for gasification. In some aspects the oxygen-containing gas can be air. In other aspects, the oxygen-containing gas can have a low nitrogen content, such as oxygen from an air separation unit or another oxygen stream including 95 vol % or more of oxygen, or 98 vol % or more, are passed into the gasifier for reaction with the solid particles comprising coke deposited on them in the coking zone.

In the gasification zone the reaction between the coke and the steam and the oxygen-containing gas produces a hydrogen and carbon monoxide-containing fuel gas and a partially gasified residual coke product. Conditions in the gasifier are selected accordingly to generate these products. Steam and oxygen rates (as well as any optional $CO_2$ rates) will depend upon the rate at which cold coke enters from the reactor and to a lesser extent upon the composition of the coke which, in turn will vary according to the composition of the heavy oil feed and the severity of the cracking conditions in the reactor with these being selected according to the feed and the range of liquid products which is required. The fuel gas product from the gasifier may contain entrained coke solids and these are removed by cyclones or other separation techniques in the gasifier section of the unit; cyclones may be internal cyclones in the main gasifier vessel itself or external in a separate, smaller vessel as described below. The fuel gas product is taken out as overhead from the gasifier cyclones. The resulting partly gasified solids are removed from the gasifier and introduced directly into the coking zone of the coking reactor at a level in the dilute phase above the lower dense phase.

Oligomerization of Olefins to Liquids

In some aspects, the liquid yield from fluidized coking (such as Flexicoking™) can be enhanced by integrating the fluidized coking process with a process for conversion of olefins to gasoline and/or aromatics. The feed to the olefin conversion process can correspond to light ends that are formed during the fluidized coking reaction. Both the liquid products and light ends from fluidized coking can be withdrawn from the coking reactor by any convenient method. If necessary, the light ends can then be separated from the liquid ($C_{5+}$) products to generate the feed for olefin oligomerization.

During olefin oligomerization, larger compounds can be synthesized from smaller olefins. Because the olefins from the coker effluent can typically have little or no organic sulfur content, the resulting oligomerization product can correspond to a low sulfur product, such as a low sulfur naphtha boiling range fraction (gasoline), a low sulfur diesel boiling range fraction, or a low sulfur aromatics fraction. Thus, a fuel fraction generated by oligomerization can correspond to a fraction that does not require further hydroprocessing prior to incorporation into a fuel pool.

Depending on the aspect, various cut points can be used for separating light ends from liquid products, so the light ends can potentially correspond to a $C_{5-}$ stream, a $C_{4-}$ stream, or a $C_{3-}$ stream. In this discussion, a $C_{4-}$ stream is defined as a hydrocarbon-containing stream where 90 vol % or more of the hydrocarbons in the stream, relative to the volume of the hydrocarbons, correspond to $C_{4-}$ hydrocarbons (e.g., butane/butene or smaller). In other words, less than 10 vol % of the hydrocarbons in a $C_{4-}$ stream correspond to $C_{5+}$ hydrocarbons. Thus, a $C_{4-}$ stream can include a minor portion of $C_5$ or larger hydrocarbons, while a $C_{5-}$ stream can include a minor portion of $C_6$ or larger hydrocarbons. It is noted that under this definition, any stream that qualifies as a $C_{4-}$ stream also qualifies as a $C_{5-}$ stream. Due to the nature of fluidized coking, which is based on thermal cracking, a portion of the $C_{2+}$ hydrocarbons in the light ends portion of the coker effluent can correspond to olefins. Thus, the light ends can be referred to as an olefin-containing stream. Optionally, a hydrocarbon-containing stream can correspond to a stream that contains 10 vol % or more of hydrocarbons.

In various aspects, the olefin-containing light ends stream from the coker can be exposed to an acidic catalyst (such as a zeolite) under effective conversion conditions for olefinic oligomerization. Optionally, the zeolite or other acidic catalyst can also include a hydrogenation functionality, such as a Group VIII metal or other suitable metal that can activate hydrogenation/dehydrogenation reactions.

Oligomerization catalysts suitable for use in olefin conversion can include the medium pore (i.e., roughly 5-7 angstroms) shape selective crystalline aluminosilicate zeolites having a silica to alumina ratio of 20:1 or greater, a constraint index of 1-12, and acid cracking activity (alpha value) of 2-200, or 2-50, or 2-10.

The acidic catalyst used in the processes described herein can be any alumina-containing catalyst, such as a zeolite-based catalyst. For example, the acidic catalyst can comprise an acidic zeolite in combination with a binder or matrix material such as alumina, silica, or silica-alumina, and optionally further in combination with a hydrogenation metal. More generally, the acidic catalyst can correspond to a molecular sieve (such as a zeolite) in combination with a binder, and optionally a hydrogenation metal. Molecular sieves for use in the catalysts can be medium pore size zeolites, such as those having the framework structure of ZSM-5, ZSM-11, ZSM-12, ZSM-22, ZSM-23, ZSM-35, ZSM-48, or MCM-22. Such molecular sieves can have a 10-member ring as the largest ring size in the framework structure. The medium pore size zeolites are a well-recognized class of zeolites and can be characterized as having a Constraint Index of 1 to 12. Constraint Index is determined as described in U.S. Pat. No. 4,016,218 incorporated herein by reference. Catalysts of this type are described in U.S. Pat. Nos. 4,827,069 and 4,992,067 which are incorporated herein by reference and to which reference is made for further details of such catalysts, zeolites and binder or matrix materials.

Additionally or alternately, catalysts based on large pore size framework structures (12-member rings) such as the synthetic faujasites, especially zeolite Y, such as in the form of zeolite USY. Zeolite beta may also be used as the zeolite component. Other materials of acidic functionality which may be used in the catalyst include the materials identified as MCM-36 and MCM-49. Still other materials can include other types of molecular sieves having suitable framework structures, such as silicoaluminophosphates (SAPOs), aluminosilicates having other heteroatoms in the framework structure, such as Ga, Sn, or Zn, or silicoaluminophosphates having other heteroatoms in the framework structure. Mordenite or other solid acid catalysts can also be used as the catalyst.

While suitable zeolites having a coordinated metal oxide to silica molar ratio of 20:1 to 200:1 or higher may be used, it can be advantageous to employ aluminosilicate ZSM-5 having a silica:alumina molar ratio of 25:1 to 70:1, suitably modified. A typical zeolite catalyst component having Bronsted acid sites can comprises, consist essentially of, or consist of crystalline aluminosilicate having the structure of ZSM-5 zeolite with 5 to 95 wt. % silica, clay and/or alumina binder.

The zeolitic catalysts can be employed in their acid forms, ion-exchanged or impregnated with one or more suitable metals, such as Ga, Pd, Zn, Ni, Co, Mo, P, and/or other metals of Periodic Groups III to VIII. The zeolite may include other components, generally one or more metals of group IB, IIB, IIIB, VA, VIA or VIIIA of the Periodic Table (IUPAC).

Useful hydrogenation components can include the noble metals of Group VIIIA, such as platinum, but other noble metals, such as palladium, gold, silver, rhenium or rhodium, may also be used. Base metal hydrogenation components may also be used, such as nickel, cobalt, molybdenum, tungsten, copper or zinc.

The catalyst materials may include two or more catalytic components which components may be present in admixture or combined in a unitary multifunctional solid particle.

In addition to the preferred aluminosilicates, the gallosilicate, ferrosilicate and "silicalite" materials may be employed. ZSM-5 zeolites can be useful in the process because of their regenerability, long life and stability under the extreme conditions of operation. Usually the zeolite crystals have a crystal size from 0.01 to over 2 microns or more, such as 0.02-1 micron. As an example of a suitable catalyst for olefin conversion, the olefin conversion can be performed under fluidized bed conditions with catalyst particles that contain 25 wt. % to 40 wt. % H-ZSM-5 zeolite, based on total catalyst weight, contained within a silica-alumina matrix. Typical Alpha values for the catalyst can be 100 or less. The Alpha Test is described in U.S. Pat. No. 3,354,078, and in the Journal of Catalysis, Vol. 4, p. 527 (1965); Vol. 6, p. 278 (1966); and Vol. 61, p. 395 (1980), each incorporated herein by reference as to that description.

In various aspects, the olefin-containing feed may be exposed to the acidic catalyst by using a moving or fluid catalyst bed reactor. In such aspects, the catalyst may be regenerated, such via continuous oxidative regeneration. The extent of coke loading on the catalyst can then be continuously controlled by varying the severity and/or the frequency of regeneration. In a turbulent fluidized catalyst bed the conversion reactions are conducted in a vertical reactor column by passing hot reactant vapor upwardly through the reaction zone and/or reaction vessel at a velocity greater than dense bed transition velocity and less than transport velocity for the average catalyst particle. A continuous process is operated by withdrawing a portion of coked catalyst from the reaction zone and/or reaction vessel, oxidatively regenerating the withdrawn catalyst and returning regenerated catalyst to the reaction zone at a rate to control catalyst activity and reaction severity to effect feedstock conversion. Preferred fluid bed reactor systems are described in Avidan et al U.S. Pat. No. 4,547,616; Harandi & Owen U.S. Pat. No. 4,751,338; and in Tabak et al U.S. Pat. No. 4,579,999, incorporated herein by reference. In other aspects, other types of reactors can be used, such as fixed bed reactors, riser reactors, fluid bed reactors, and/or moving bed reactors.

Conversion of lower olefins, especially ethene, propene and butenes, over H-ZSM-5 (and/or other zeolitic catalysts as described above) is effective at moderately elevated temperatures and pressures. The conversion products are sought as liquid fuels, especially the $C_{5+}$ hydrocarbons. Product distribution for liquid hydrocarbons can be varied by controlling process conditions, such as temperature, pressure and space velocity. Olefinic gasoline (e.g., $C_5$-$C_9$) is readily formed at elevated temperature (e.g., 175° C. to 450° C., or 200° C. to 400° C.) and moderate pressure from ambient to 5500 kPa-a, preferably 250 kPa-a to 2900 kPa-a. A wide range of weight hourly space velocities (WHSV) of olefin versus catalyst can be suitable, such as space velocities of 0.1 $hr^{-1}$ to 80 $hr^{-1}$. Under appropriate conditions of catalyst activity, reaction temperature and space velocity, predominantly olefinic gasoline can be produced in good yield and may be recovered as a product. Operating details for typical olefin oligomerization units are disclosed in U.S. Pat. Nos. 4,456,779; 4,497,968 (Owen et al.) and U.S. Pat. No. 4,433,185 (Tabak), incorporated herein by reference.

After olefin oligomerization, the resulting effluent from the reaction can be separated to form a $C_{5+}$ product fraction and a light ends by-product ($C_{4-}$) that has an increased concentration of paraffins relative to the feed to the olefin conversion process. This paraffin-enriched light ends fraction can, for example, be recycled for addition to a heated conduit in the fluidized coking. The heated conduit can provide suitable conditions for conversion of a portion of the paraffins to olefins. Because the paraffins in the light ends can correspond to roughly 5 wt % of the initial feed for coking, the ability to convert paraffins to olefins can provide a substantial additional boost to the net liquid yield. Of course, a portion of the light ends can be vented or purged from the system, to prevent accumulation of any methane that may be generated during coking.

Configuration Examples: Increased Liquids Production Via Olefin Oligomerization

Figure 3:
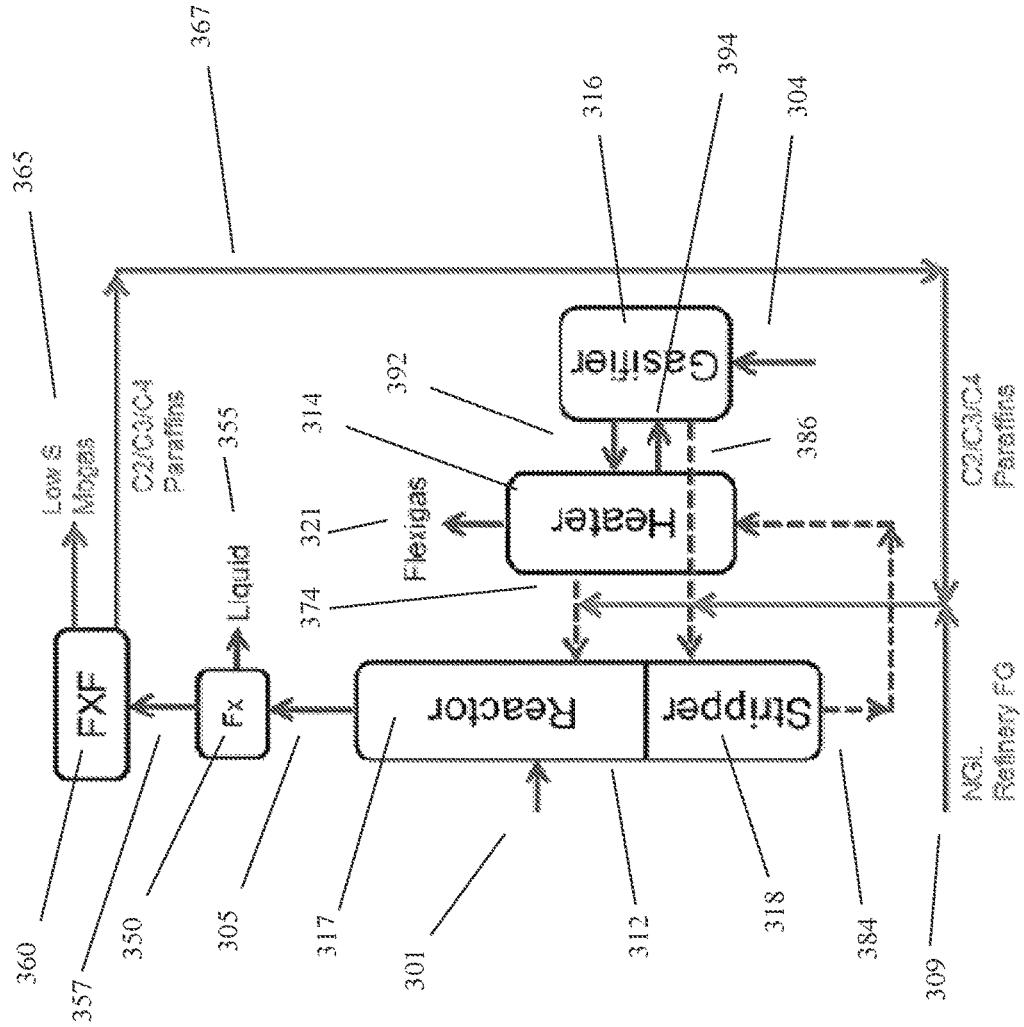
FIG. 3 shows an example of a fluidized bed coking system including an integrated gasifier and an integrated oligomerization stage for improving liquid yields.
Figure 4:
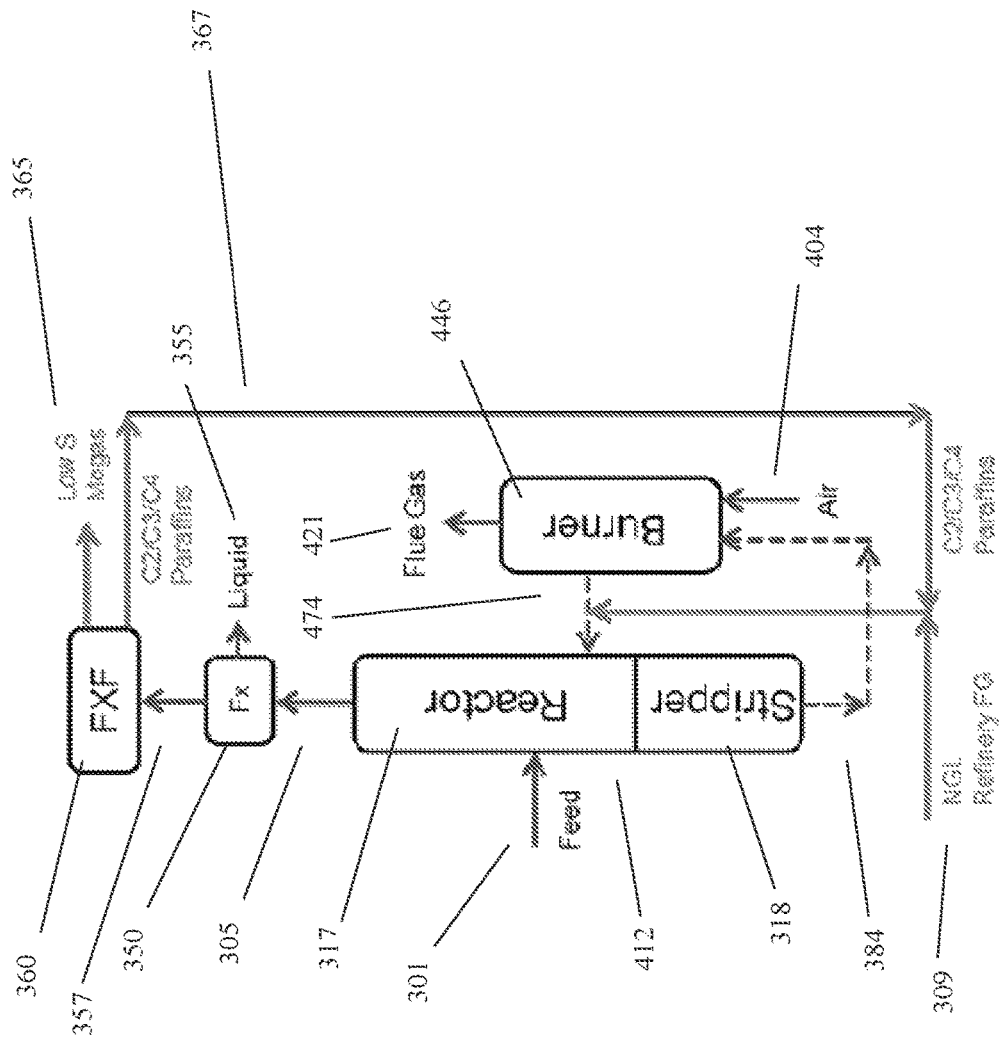
FIG. 4 shows another example of a fluidized bed coking system including an integrated oligomerization stage for improving liquid yields.

FIGS. 3 and 4 show examples of configurations that can provide an integrated fluidized bed coker and gasifier (or other coke combustion stage) along with an olefin oligomerization stage to allow for increased production of liquid ($C_{5+}$) products. FIG. 3 shows an example of a configuration that includes an integrated gasifier, while FIG. 4 shows an example of a configuration where a fluidized coker is integrated with a burner as the coke combustion stage.

In FIG. 3, a feed 301 suitable for coking is introduced into fluidized bed coker 312. The reactor or coking section 317 and stripper section 318 of fluidized bed coker 312 are shown in FIG. 3. The feed 301 can correspond to a heavy oil feed, or any other convenient feed typically used as an input for a coker. In the configuration shown in FIG. 3, the fluidized bed coker 312 is integrated with a heater 314 and a gasifier 316. This combination of elements is similar to the configuration shown in FIG. 1. In other aspects, the fluidized bed coker can be integrated with a gasifier without having an intermediate heater.

In FIG. 3, fluidized bed coker 312 generates a coker effluent 305 that includes fuel boiling range liquids generated during the coking process. Heat for coker 312 can be provided by hot coke recycle line 374 from heater 314 and/or second hot coke recycle line 386 from gasifier 316. In the configuration shown in FIG. 3, the hot coke recycle line 374 from heater 314 is passed into coking section 317 of coker 312. The second hot coke recycle line 386 from gasifier 316 is passed into stripping section 318 of coker 312. This can provide separate control of the heating in the coking section 317 and stripping section 318 of coker 312. In other aspects, any convenient number and combination of hot coke recycle lines from heater 314 and/or gasifier 316 can be used to provide heat to coker 312. It is noted that paraffin recycle stream 367 and/or additional paraffins 309 from natural gas or refinery fuel gas can be introduced into either a hot coke recycle line 374 from heater 314 or a hot coke recycle line 386 from gasifier 316 while still achieving conversion of a portion of the paraffins to olefins.

Cold coke from coker 312 is passed into heater 314 via line 384. Coke from heater 314 is transferred to gasifier 316 through line 394 and hot, partly gasified particles of coke are circulated from the gasifier back to the coker 312 through line 386. As noted above, line 386 could instead be passed into heater 314, and then heater 314 could provide both hot coke lines to reactor 312. Fuel gas generated in gasifier 316 is returned to heater 314 via line 392 and then exits as fuel gas stream 321. It is noted that gasifier 316 does not generate a slag that is separately removed from the gasifier. Instead, excess coke is withdrawn from the heater 314 and/or gasifier 316 (not shown). Oxygen and steam for the gasifier are introduced, for example, via line 304.

Coker effluent 305 from the coker 312 can then be passed into a separation stage 350 for separation of a liquid product 355 from a light ends or gas phase product 357. The light ends product 357 can then be passed into oligomerization stage 360 to produce oligomerized products 365. For example, the oligomerized products can correspond to a (low sulfur) naphtha boiling range product. The oligomerization stage 360 can also produce a light ends product 367. This oligomerization light ends product can include $C_2$-$C_4$ paraffins as well as small olefins that did not react in the oligomerization stage 360. This stream can be recycled to a hot coke return line, such as hot coke return line 374 second hot coke return line 386, for conversion of at least a portion of the paraffins into additional olefins. Such olefins can then exit from the coker and be recycled back to the olefin oligomerization stage for further formation of liquid products. Optionally, still further liquid products can be generated by introducing other streams 309 containing $C_2$-$C_4$ paraffins into a hot coke return line 374 or 386, such as natural gas liquids or refinery fuel gas.

Many of the configuration elements in FIG. 4 are similar to the elements in FIG. 3. However, instead of having an integrated gasifier, FIG. 4 shows a fluidized coking system with a conventional burner 446 to provide heat for coker 412. Solid particles with deposited coke are provided to burner 446 via cold coke line 384, while a burner hot coke return line 474 allows heated particles to be returned to coker 412. The amount of oxygen introduced into burner 446 is typically greater than in a gasifier, so the flue gas 421 generated by burner 446 has a higher content of $CO_2$ relative to CO. For a conventional burner 446, additional steam is not needed, so the input gas can correspond to air 404.

As an example of formation of liquids from the olefins in a coker effluent, a pilot scale configuration was used to convert olefins to gasoline (i.e., naphtha boiling range products). A light ends feed separated from a coker effluent was exposed to an olefin oligomerization catalyst at a reaction temperature of between ~400° C. and ~450° C. The reactor pressure was 50 psig (~340 kPa-g) and the weight hourly space velocity of olefins in the feed to catalyst was 0.38 $hr^{-1}$. The catalyst corresponded to alumina bound ZSM-5 with an alpha value of 3-4. The yields from once-through conversion of the light ends feed are shown in Table 3.

TABLE 3

Once Through Conversion of Olefins to $C_{5+}$ Gasoline

| Conversion Product | Yield (wt % relative to olefin feed) |
| --- | --- |
| $C_{5+}$ Gasoline | 60 |
| Butenes | 5 |
| Isobutane | 12 |
| n-butane | 7 |
| $C_3$ | 13 |
| $C_2$ | 3 |

The $C_{5+}$ gasoline had a Research Octane Number (RON) of 97-98 and a Motor Octane Number (MON) of 84-85, as determined by ASTM D2699 and D2700, respectively. It is believed that the yields and octane numbers from this once-through processing are representative of the yields and octanes that would be achieved after inclusion of additional olefins that are generated by paraffin recycle via hot coke return conduits.

Methanol Production

In addition to or as an alternative to performing olefin oligomerization on the light ends from the primary coking reactor, the flue gas or fuel gas from an integrated gasifier in a fluidized coking system can also be used to form additional liquid products. Based on the higher temperature conditions in the gasifier, the fuel gas can have a reduced or minimized content of hydrocarbons. Instead, the components for further reaction to form liquids in the fuel gas can correspond to $H_2$ and CO. Although this flue gas is generated in the gasifier, it is noted that the withdrawal location for the fuel gas may correspond to the heater and/or a dedicated separation vessel associated with the gasifier.

After withdrawing the fuel gas from the heater or gasifier, the fuel gas can undergo further processing to produce a stream with an increased concentration of CO and $H_2$. In aspects where air is introduced into the gasifier as the source of oxygen, part of the separation can correspond to a nitrogen wash. The nitrogen content of the fuel gas can correspond to 50 vol % or more of the stream. Reducing the amount of this diluent can be beneficial for the subsequent methanol production process. In other aspects where a reduced or minimized amount of nitrogen was introduced into the gasifier as part of the oxygen stream, the amount of nitrogen in the fuel gas can also be minimal, such as 5 vol % or less. At this level, the nitrogen can be passed into a methanol synthesis process without requiring separation.

Other gases present in the fuel gas can be separated to improve the subsequent methanol synthesis process. For example, the gasification conditions can result in formation of a substantial amount of $CO_2$, corresponding to 5 vol % to 20 vol % of the fuel gas. This $CO_2$ can be removed from the fuel gas by any convenient method. Suitable methods for separation of $CO_2$ from the fuel gas can include, but are not limited to, amine washing and cryogenic separation. After separation of the CO₂ from the fuel gas, the CO₂ can be recovered (if necessary) and then used as in any convenient manner. In some aspects (such as aspects where an air separation unit is used to generate a high purity oxygen stream for use in the gasifier), at least a portion of the CO₂ can be used as a diluent for the gasification process. As discussed further below, CO₂ can potentially be converted to methanol under the methanol synthesis conditions, so complete removal of CO₂ is not necessary.

Another gas present in the fuel gas can be H₂S. For many types of heavy petroleum feeds, the feed can include a substantial amount of sulfur. This sulfur can be incorporated into the coke and then converted to H₂S in the gasifier. Any convenient method for removal of H₂S can be used. In aspects where an amine wash is used for CO₂ separation, the amine wash can also be effective for H₂S removal.

During methanol synthesis, carbon monoxide and hydrogen can react over a catalyst to produce methanol. Commercial methanol synthesis catalysts can be highly selective, with selectivities of greater than 99.8% possible under optimized reaction conditions. Typical reaction conditions can include pressures of 5 MPa to 10 MPa and temperatures of 250° C. to 300° C. With regard to the syngas input for methanol synthesis, the preferred ratio of H₂ to CO (~2:1 H₂:CO) does not match the typical ratio generated by a gasifier. However, catalysts that facilitate methanol formation from syngas can sometimes additionally facilitate the water-gas shift reaction. As a result, the reaction scheme below shows that CO₂ can also be used to form methanol:

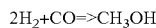

$$2H_2 + CO \Rightarrow CH_3OH$$

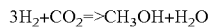

$$3H_2 + CO_2 \Rightarrow CH_3OH + H_2O$$

For methanol synthesis reactions, the composition of the synthesis gas input can be characterized by the Module value M:

$$M = [H_2 - CO_2]/[CO + CO_2]$$

Module values close to 2 can generally be suitable for production of methanol, such as values of M that are at least 1.7, or at least 1.8, or at least 1.9, and/or less than 2.3, or less than 2.2, or less than 2.1. As can be noted from the Module Value equation above, in addition to the ratio of H₂ to CO, the ratio of CO to CO₂ in the syngas can impact the reaction rate of the methanol synthesis reaction.

The output stream from a gasifier can contain relatively high concentrations of H₂, CO, CO₂, and water. Through a combination of separations, (reverse) water gas shift reactions, and/or other convenient mechanisms, the composition of the fuel gas from the gasifier and/or a stream derived/withdrawn from the fuel gas can be adjusted. The adjustment of the composition can include removing excess water and/or CO₂, adjusting the ratio of H₂:CO, adjusting the Module value M, or a combination thereof. For example, a typical fuel gas from the gasifier may have an H₂:CO ratio of roughly 1:1. Removal of CO₂ from the fuel gas can facilitate a subsequent water gas shift reaction to increase this ratio to closer to 2:1 and/or to increase the Module value M of the stream to closer to 2.

In a typical methanol plant, a large percentage of the reactor exhaust can be recycled after recovery of methanol liquid, due to low conversion per pass. In some configurations, the output from the methanol synthesis reaction can be separated into a liquid alcohol product, a recycle syngas stream, and a vented purge. The vented purge can contain syngas components, fuel components (e.g. methane), and inerts. At least a portion of the vented purge can be used to raise steam for heating the syngas production.

Methanol Conversion

After forming methanol, the methanol can be converted to liquid products. Any convenient type of methanol conversion process can be used. Examples of suitable methanol conversion processes include various processes for conversion of methanol to gasoline, aromatics, and/or olefins. It is noted that some reaction schemes for conversion of methanol to gasoline and/or aromatics can proceed via an olefin intermediate. Thus, the catalyst for methanol conversion can potentially be similar to a catalyst used for olefin oligomerization.

Suitable and/or effective conditions for performing a methanol conversion reaction can include average reaction temperatures of 300° C. to 550° C. (or 350° C. to 550° C., or 400° C. to 500° C.), total pressures between 10 psig (~70 kPag) to 400 psig (~2700 kPag), or 50 psig (~350 kPag) to 350 psig (~2400 kPag), or 100 psig (~700 kPag) to 300 psig (~2100 kPag), and an oxygenate space velocity between 0.1 h⁻¹ to 10 h⁻¹ based on weight of oxygenate relative to weight of catalyst. For example, the average reaction temperature can be at least 300° C., or at least 350° C., or at least 400° C., or at least 450° C. Additionally or alternately, the average reaction temperature can be 550° C. or less, or 500° C. or less, or 450° C. or less, or 400° C. or less. In this discussion, average reaction temperature is defined as the average of the temperature at the reactor inlet and the temperature at the reactor outlet for the reactor where the conversion reaction is performed. As another example, the total pressure can be at least 70 kPag, or at least 350 kPag, or at least 500 kPag, or at least 700 kPag, or at least 1000 kPag. Additionally or alternately, the total pressure can be 3000 kPag or less, or 2700 kPag or less, or 2400 kPag or less, or 2100 kPag or less.

Optionally, a portion of the conversion effluent can be recycled for inclusion as part of the feed to the conversion reactor. For example, at least a portion of the light ends from the conversion effluent can be recycled as part of the feed. The recycled portion of the light ends can correspond to any convenient amount, such as 25 wt % to 75 wt % of the light ends. Recycling of light ends can provide olefins, which can serve as an additional reactant in the conversion reaction, as well as providing a mechanism for temperature control.

Various types of reactors can provide a suitable configuration for performing a conversion reaction. Suitable reactors can include moving bed reactors (such as riser reactors), and fluidized bed reactors.

A suitable zeolite can include a 10-member or 12-member ring pore channel network, such as a 1-dimensional 10-member ring pore channel or a 3-dimensional 10-member ring pore channel. Examples of suitable zeolites having a 3-dimensional 10-member ring pore channel network include zeolites having an MFI or MEL framework, such as ZSM-5 or ZSM-11. ZSM-5 is described in detail in U.S. Pat. Nos. 3,702,886 and Re. 29,948. ZSM-11 is described in detail in U.S. Pat. No. 3,709,979. Preferably, the zeolite is ZSM-5. Examples of suitable zeolites having a 1-dimensional 10-member ring pore channel network include zeolites having a MRE (ZSM-48), MTW, TON, MTT, and/or MFS framework. In some aspects, a zeolite with a 3-dimensional pore channel can be preferred for conversion of methanol, such as a zeolite with an MFI framework.

Generally, a zeolite having desired activity for methanol conversion can have a silicon to aluminum molar ratio of 10 to 200, or 15 to 100, or 20 to 80, or 20 to 40. For example, the silicon to aluminum ratio can be at least 10, or at least 20, or at least 30, or at least 40, or at least 50, or at least 60. Additionally or alternately, the silicon to aluminum ratio can be 300 or less, or 200 or less, or 100 or less, or 80 or less, or 60 or less, or 50 or less.

Typically, reducing the silicon to aluminum ratio in a zeolite will result in a zeolite with a higher acidity, and therefore higher activity for cracking of hydrocarbon or hydrocarbonaceous feeds, such as petroleum feeds. However, with respect to conversion of oxygenates to aromatics, such increased cracking activity may not be beneficial, and instead may result in increased formation of residual carbon or coke during the conversion reaction. Such residual carbon can deposit on the zeolite catalyst, leading to deactivation of the catalyst over time. Having a silicon to aluminum ratio of at least 40, such as at least 50 or at least 60, can reduce or minimize the amount of additional residual carbon that is formed due to the acidic or cracking activity of a catalyst.

It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

Additionally or alternately, a zeolitic catalyst can include and/or be enhanced by a transition metal. Preferably the transition metal is a Group 12 metal from the IUPAC periodic table (sometimes designated as Group IIB) selected from Zn, Cd, or a combination thereof. More generally, the transition metal can be any convenient transition metal selected from Groups 6-15 of the IUPAC periodic table. The transition metal can be incorporated into the zeolite/catalyst by any convenient method, such as by impregnation, by ion exchange, by mulling prior to extrusion, and/or by any other convenient method. Optionally, the transition metal incorporated into a zeolite/catalyst can correspond to two or more metals. After impregnation or ion exchange, the transition metal-enhanced catalyst can be treated in air or an inert atmosphere at a temperature of 400° C. to 700° C. The amount of transition metal can be expressed as a weight percentage of metal relative to the total weight of the catalyst (including any zeolite and any binder). A catalyst can include 0.05 wt % to 20 wt % of one or more transition metals, or 0.1 wt % to 10 wt %, or 0.1 wt % to 5 wt %, or 0.1 wt % to 2.0 wt %. For example, the amount of transition metal can be at least 0.1 wt % of transition metal, or at least 0.25 wt % of transition metal, or at least 0.5 wt %, or at least 0.75 wt %, or at least 1.0 wt %. Additionally or alternately, the amount of transition metal can be 20 wt % or less, or 10 wt % or less, or 5.0 wt % or less, or 2.0 wt % or less, or 1.5 wt % or less, or 1.2 wt % or less, or 1.1 wt % or less, or 1.0 wt % or less.

In some optional aspects, a zeolitic catalyst can be substantially free of phosphorous. A catalyst composition that is substantially free of phosphorous can contain 0.01 wt % of phosphorous or less, such as less than 0.005 wt % of phosphorous, or less than 0.001 wt % of phosphorous. A zeolitic catalyst that is substantially free of phosphorous can be substantially free of intentionally added phosphorous or substantially free of both intentionally added phosphorous as well as phosphorous present as an impurity in a reagent for forming the catalyst composition. In some aspects, a zeolitic catalyst can contain no added phosphorous, such as containing no intentionally added phosphorous and/or containing no phosphorous impurities to within the detection limits of standard methods for characterizing a reagent and/or a resulting zeolite.

Optionally, a zeolitic catalyst for methanol conversion can include added phosphorus, such as phosphorus added by impregnation, ion exchange, mulling prior to extrusion, or another convenient method. The amount of phosphorus can be related to the amount of transition metal in the catalyst composition. In some aspects, the molar ratio of phosphorus to transition metal can be 0.5 to 5.0, or 1.5 to 3.0, or 1.0 to 2.5, or 1.5 to 2.5. At higher molar ratios of phosphorus to transition metal, the phosphorus can be beneficial for maintaining a relatively stable selectivity for aromatics formation during an oxygenate conversion process. Additionally or alternately, a catalyst can include 0.05 wt % to 10 wt % of phosphorus, or 0.1 wt % to 10 wt %, or 0.1 wt % to 5 wt %, or 0.1 wt % to 2.0 wt %. For example, the amount of phosphorus can be at least 0.1 wt %, or at least 0.25 wt %, or at least 0.5 wt %, or at least 0.75 wt %, or at least 1.0 wt %. Additionally or alternately, the amount of phosphorus can be 10 wt % or less, or 5 wt % or less, or 2.0 wt % or less, or 1.5 wt % or less, or 1.2 wt % or less, or 1.1 wt % or less, or 1.0 wt % or less.

A catalyst composition can employ a transition metal-enhanced zeolite in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Preferably, the transition metal can be incorporated after formulation of the zeolite (such as by extrusion) to form self-bound catalyst particles. Optionally, a self-bound catalyst can be steamed after extrusion. The terms "unbound" and "self-bound" are intended to be synonymous and mean that the present catalyst composition is free of any of the inorganic oxide binders, such as alumina or silica, frequently combined with zeolite catalysts to enhance their physical properties.

The transition metal-enhanced zeolite catalyst composition employed herein can further be characterized based on activity for hexane cracking, or Alpha value. Alpha value is a measure of the acid activity of a zeolite catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of ~538° C. and a variable flow rate as described in detail in the Journal of Catalysis, Vol. 61, p. 395. Higher alpha values correspond with a more active cracking catalyst. For an oxygenate conversion catalyst, Alpha values of at least 15 can be suitable, with alpha values greater than 100 being preferred. In particular, the Alpha value can be 15 to 1000, or 50 to 1000, or 100 to 1000.

As an alternative to forming self-bound catalysts, zeolite crystals can be combined with a binder to form bound catalysts. Suitable binders for zeolite-based catalysts can include various inorganic oxides, such as silica, alumina, zirconia, titania, silica-alumina, cerium oxide, magnesium oxide, yttrium oxide, or combinations thereof. For catalysts including a binder, the catalyst can comprise at least 10 wt % zeolite, or at least 30 wt %, or at least 50 wt %, such as up to 90 wt % or more. Generally, a binder can be present in an amount between 1 wt % and 90 wt %, for example between 5 wt % and 40 wt % of a catalyst composition. In some aspects, the catalyst can include at least 5 wt % binder, such as at least 10 wt %, or at least 20 wt %. Additionally or alternately, the catalyst can include 90 wt % or less of binder, such as 50 wt % or less, or 40 wt % or less, or 35 wt % or less. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

In some aspects, a binder can be used that is substantially free of alumina, such as a binder that is essentially free of alumina. In this description, a binder that is substantially free of alumina is defined as a binder than contains 10 wt % alumina or less, such as 7 wt % or less, or 5 wt % or less, or 3 wt % or less. A binder that is essentially free of alumina is defined as a binder that contains 1 wt % or less, such as 0.5 wt % or less, or 0.1 wt % or less. In still other aspects, a binder can be used that contains no intentionally added alumina and/or that contains no alumina within conventional detection limits for determining the composition of the binder and/or the reagents for forming the binder. Although alumina is commonly used as a binder for zeolite catalysts, due in part to ease of formulation of alumina-bound catalysts, in some aspects the presence of alumina in the binder can reduce or inhibit the activity of a transition metal-enhanced zeolite for converting methanol to aromatics. For example, for a catalyst where the transition metal is incorporated into the catalyst after formulation of the bound catalyst (such as by extrusion), the transition metal may have an affinity for exposed alumina surfaces relative to exposed zeolite surfaces, leading to increased initial deposition and/or migration of transition metal to regions of the bound catalyst with an alumina surface in favor of regions with a zeolite surface. Additionally or alternately, alumina-bound catalysts can tend to have low micropore surface area, meaning that the amount of available zeolite surface available for receiving a transition metal may be undesirably low.

Figure 5:
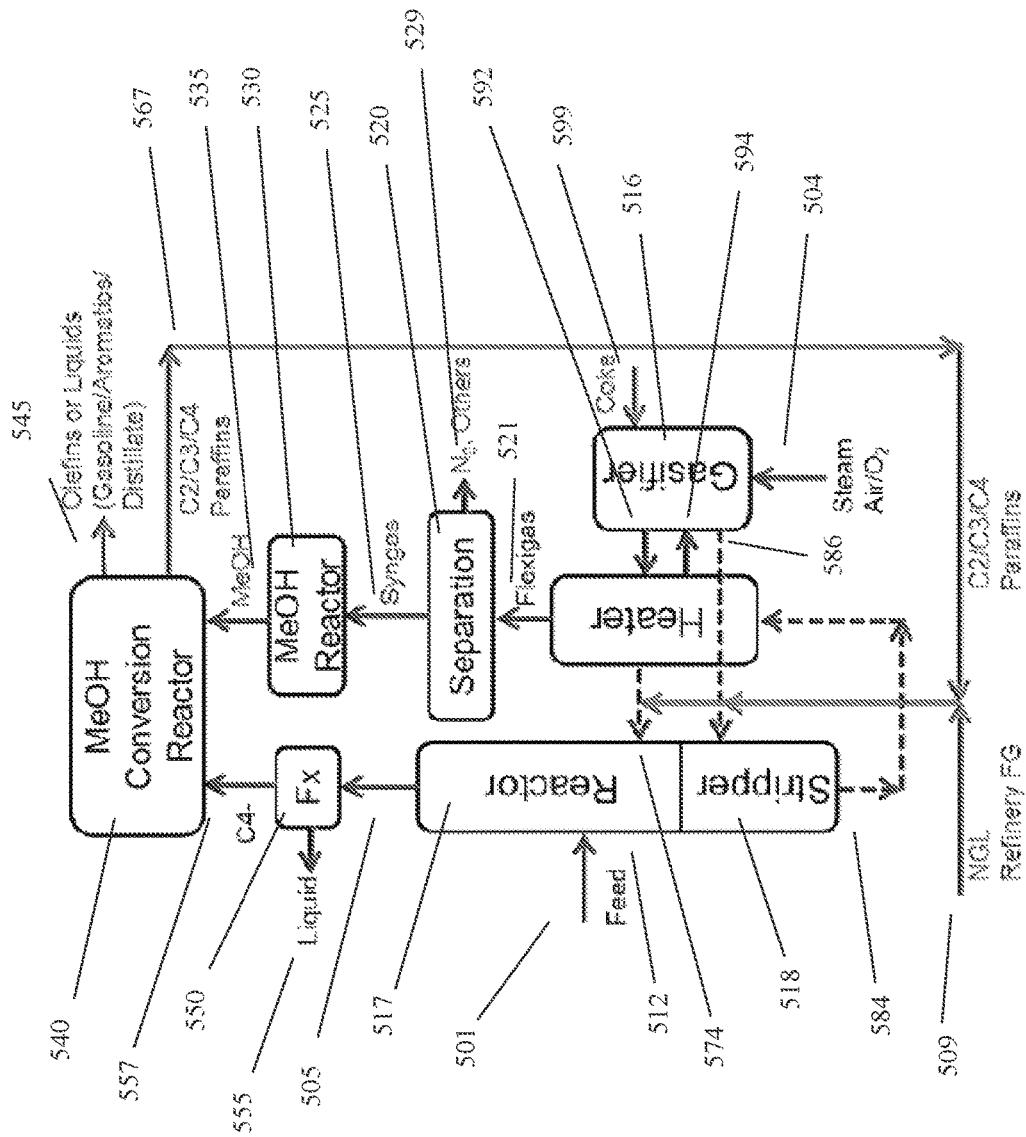
FIG. 5 schematically shows an example of a configuration for integrating fluidized coking with production of additional liquids via production of methanol derived at least in part from a synthesis gas.

Configuration Examples: Increased Liquids Production Via Synthesis of Methanol Intermediate FIG. 5 shows an example of a configuration that can provide an integrated fluidized bed coker and gasifier along with methanol synthesis. In FIG. 5, a feed 501 suitable for coking is introduced into fluidized bed coker 512. The reactor or coking section 517 and stripper section 518 of fluidized bed coker 512 are shown in FIG. 5. The feed 501 can correspond to a heavy oil feed, or any other convenient feed typically used as an input for a coker. In the configuration shown in FIG. 5, the fluidized bed coker 512 is integrated with a heater 514 and a gasifier 516. This combination of elements is similar to the configuration shown in FIG. 1. In other aspects, the fluidized bed coker can be integrated with a gasifier without having an intermediate heater.

In FIG. 5, fluidized bed coker 512 generates a coker effluent 505 that includes fuel boiling range liquids generated during the coking process. Heat for coker 512 can be provided by hot coke recycle line 574 from heater 514 and/or second hot coke recycle line 586 from gasifier 516. In the configuration shown in FIG. 5, the hot coke recycle line 574 from heater 514 is passed into coking section 517 of coker 512. The second hot coke recycle line 586 from gasifier 516 is passed into stripping section 518 of coker 512. This can provide separate control of the heating in the coking section 517 and stripping section 518 of coker 512. In other aspects, any convenient number and combination of hot coke recycle lines from heater 514 and/or gasifier 516 can be used to provide heat to coker 512. It is noted that paraffin recycle stream 567 and/or additional paraffins 509 from natural gas or refinery fuel gas can be introduced into either a hot coke recycle line 574 or second hot coke recycle line 386 while still achieving conversion of a portion of the paraffins to olefins.

Cold coke from coker 512 is passed into heater 514 via line 584. Coke from heater 514 is transferred to gasifier 516 through line 594 and hot, partly gasified particles of coke are circulated from the gasifier back to the coker 512 through line 586. As noted above, line 586 could instead be passed into heater 514, and then heater 514 could provide both hot coke lines to reactor 512. Fuel gas generated in gasifier 516 is returned to heater 514 via line 592. It is noted that gasifier 516 does not generate a slag that is separately removed from the gasifier. Instead, excess coke is withdrawn from the heater 514 and/or gasifier 516 (not shown). Oxygen (such air) and steam for the gasifier are introduced, for example, via line 504.

Fuel gas provided from gasifier 516 to heater 514 via line 592 can provide the fluidization needed in heater 514. The fuel gas can be withdrawn from heater 514 via line 521, optionally after passing through cyclone separators (not shown) for removal of coke fines from the fuel gas. The fuel gas in line 521 can be passed into a separation stage 520 for separation of $CO_2$ and optionally $N_2$ from the fuel gas. Optionally, separation stage 520 can also be used for removal of $H_2S$ from the fuel gas stream 521. Optionally, one or more additional separation stages may be present if removal of any other impurities from fuel gas stream 521 is desired. After separation of $CO_2$ (and/or other impurities), the remaining portion of the fuel gas stream can correspond to a synthesis gas stream 525. The synthesis gas stream 525 can be passed into a methanol synthesis plant 530 for production of methanol 535.

Methanol 535 can then be passed into a methanol conversion reactor 540. Optionally, an olefin-containing light ends stream 557 that is separated from coker effluent 505 in separation stage 550 can also be passed into the methanol conversion reactor 540. The olefins from the light ends stream 557 can contribute to formation of liquids under the methanol conversion conditions. The separation in separation stage 550 also produces a liquid product stream 555 based on the coker effluent. The methanol conversion reactor 540 can generate a liquid conversion product 545, such as a naphtha or distillate boiling range product, and a conversion light ends product 567 that includes $C_2$-$C_4$ paraffins. The conversion light ends product 567 can be recycled to a hot coke return line 574 or 586, optionally along with an additional paraffin-containing stream 509, for creation of additional olefins. Optionally, additional coke 599 can be added to gasifier 316 as another method for further increasing liquid yields.

As an example of formation of liquids from methanol, a pilot scale configuration was used to convert methanol to gasoline (i.e., naphtha boiling range products). A 100% methanol feed was exposed to an methanol catalyst at a reaction temperature of between ~370° C. and ~450° C. The reactor pressure was 25-50 psig (~170-~340 kPa-g) and the weight hourly space velocity of feed to catalyst was 0.5-1.5 $hr^{-1}$. The catalyst corresponded to alumina bound ZSM-5. The yields from once-through conversion of the methanol feed are shown in Table 4.

TABLE 4

Once Through Conversion of Methanol to $C_{5+}$ Gasoline

| Conversion Product | Yield (wt % relative to feed) |
|---|---|
| $C_{5+}$ Gasoline | 67 |
| Butenes | 5.8 |
| Isobutane | 8.5 |
| n-butane | 1.5 |
| Propylene | 5.5 |
| Propane | 3.5 |
| Ethylene | 5.4 |
| Methane and Ethane | 2.8 |

The $C_{5+}$ gasoline had a Research Octane Number (RON) of roughly 97-98 and a Motor Octane Number (MON) of roughly 84-85, as determined by ASTM D2699 and D2700, respectively. It is believed that the yields from this once-through processing are representative of the yields and octanes that would be achieved after inclusion of additional olefins that are generated by paraffin recycle via hot coke return conduits.

Additional Configurations

It is noted that further integration of a fluidized coking system with a gasifier and other synthesis processes can also be achieved. For example, FIG. 6 shows a configuration for using the fuel gas from a gasifier for methanol production, ammonia production, and/or urea production. It is noted that any convenient combination of the methanol synthesis, ammonia synthesis, and urea synthesis processes can be present independently from each other. To the degree that an output of one optional process (such as ammonia) is described as being an input for a second optional process (such as urea synthesis), it is understood that in some aspects, the input for the second optional process can be derived from another conventional source.

In FIG. 6, a feed 601 suitable for coking is introduced into fluidized bed coker 612. The feed 601 can correspond to a heavy oil feed, or any other convenient feed typically used as an input for a coker. In the configuration shown in FIG. 6, the fluidized bed coker 612 is integrated with a heater 614 and a gasifier 616. This combination of elements is similar to the configuration shown in FIG. 1.

In FIG. 6, fluidized bed coker 612 generates a coker effluent 305 that includes fuel boiling range liquids generated during the coking process. Heat for coker 612 is provided by hot coke recycle line 686, while cold coke from coker 612 is passed into heater 614 via line 684. Coke from heater 614 is transferred to gasifier 616 through line 694 and hot, partly gasified particles of coke are circulated from the gasifier back to the heater through line 696. Fuel gas generated in gasifier 616 is returned to heater 614 via line 692. It is noted that gasifier 616 does not generate a slag that is separately removed from the gasifier. Instead, excess coke is withdrawn from the heater 614 by way of line 607. Oxygen for performing gasification is introduced into gasifier 616 via line 645. It is noted that the steam lines for fluidization of the coke in the fluidized bed and the gasifier are not shown in FIG. 6.

Fuel gas provided from gasifier 616 to heater 614 via line 692 can provide the fluidization needed in heater 614. The fuel gas can be withdrawn from heater 614 via line 621, optionally after passing through cyclone separators (not shown) for removal of coke fines from the fuel gas. The fuel gas in line 621 can be passed into a separation stage 620 for separation of $CO_2$ 629 and $N_2$ 627 from the fuel gas. Optionally, separation stage 620 can also be used for removal of $H_2S$ from the fuel gas stream 621. Optionally, one or more additional separation stages may be present if removal of any other impurities from fuel gas stream 621 is desired. After separation of $CO_2$ (and/or other impurities), the remaining portion of the fuel gas stream can correspond to a synthesis gas stream 625. The synthesis gas stream 625 can be passed into a methanol synthesis plant 630 for production of methanol 635.

The nitrogen stream 627 from separation stage 620 can be passed into an ammonia synthesis process 650. By using an appropriate nitrogen wash in separation stage 620, an output nitrogen stream 627 with suitable purity for ammonia synthesis can be generated. The ammonia synthesis process 650 can also receive a hydrogen stream 665 corresponding to 98 vol % or more of hydrogen. In FIG. 6, hydrogen stream 665 is provided from a hydrogen source 660. Optionally, hydrogen stream 665 can be derived at least in part from synthesis gas stream 625. The hydrogen stream 665 and nitrogen stream 627 can be reacted in ammonia synthesis process 650 to form ammonia output 655. Optionally, a portion 671 of ammonia output 655 can be passed into a urea synthesis process 670 for production of a urea stream 675. The urea synthesis process 670 can also require a stream of $CO_2$ 673. Optionally, at least a portion of $CO_2$ stream 673 can correspond to $CO_2$ derived from $CO_2$ stream 629.

Additional Embodiments

Embodiment 1

A method for performing fluidized coking on a feed, comprising: exposing a feedstock comprising a T10 distillation point of 343° C. or more to a fluidized bed comprising solid particles in a reactor under coking conditions to form a coker effluent, the thermal cracking conditions comprising 10 wt % or more conversion of the feedstock relative to 343° C., the thermal cracking conditions being effective for depositing coke on the solid particles; introducing an oxygen-containing stream and steam into a coke combustion stage; passing at least a portion of the solid particles comprising deposited coke from the reactor to the coke combustion stage; exposing the at least a portion of the solid particles comprising deposited coke to combustion conditions to form a gas phase product comprising $H_2$, CO, and $CO_2$ and partially combusted solid particles; removing at least a first portion of the partially combusted solid particles from the coke combustion stage; passing at least a second portion of the partially combusted solid particles from the coke combustion stage to the reactor; separating the coker effluent to form a lower boiling product comprising $C_2$-$C_4$ olefins and a higher boiling product comprising a 343° C.− portion; exposing at least a portion of the lower boiling product to a catalyst under olefin oligomerization conditions to form an oligomerized product and a light ends product comprising $C_2$-$C_4$ paraffins; and introducing at least a portion of the light ends product into the second portion of the partially combusted solid particles after the second portion of the partially combusted solid particles exits from the coke combustion stage, and preferably prior to passing the second portion of the partially combusted solid particles into the reactor, wherein the coke combustion stage optionally comprises a gasifier.

Embodiment 2

A method for performing fluidized coking on a feed, comprising: exposing a feedstock comprising a T10 distillation point of 343° C. or more to a fluidized bed comprising solid particles in a reactor under coking conditions to form a coker effluent, the thermal cracking conditions comprising 10 wt % or more conversion of the feedstock relative to 343° C., the thermal cracking conditions being effective for depositing coke on the solid particles; introducing an oxygen-containing stream and steam into a gasifier; passing at least a portion of the solid particles comprising deposited coke from the reactor to the gasifier; exposing the at least a portion of the solid particles comprising deposited coke to gasification conditions in a gasifier to form a gas phase product comprising $H_2$, CO, and $CO_2$ and partially gasified solid particles; separating $CO_2$, $H_2S$, or a combination thereof from the gas phase product to form at least a synthesis gas stream; exposing at least a portion of the synthesis gas stream to a methanol synthesis catalyst under synthesis conditions to form a methanol-containing product stream; exposing at least a portion of the methanol-containing product stream to a conversion catalyst under conversion conditions to form a conversion product comprising $C_{5+}$ hydrocarbons and a light ends product comprising $C_2$-$C_4$ paraffins; removing at least a first portion of the partially gasified solid particles from the gasifier; passing at least a second portion of the partially gasified solid particles from the gasifier to the reactor; and introducing at least a portion of the light ends product into the second portion of the partially gasified solid particles after the second portion of the partially gasified solid particles exits from the gasifier, and preferably prior to passing the second portion of the partially gasified solid particles into the reactor.

Embodiment 3

The method of Embodiment 2, further comprising separating the coker effluent to form a lower boiling product comprising $C_2$-$C_4$ olefins and a higher boiling product comprising a 343° C.– portion, wherein exposing at least a portion of the methanol-containing product stream to a conversion catalyst under conversion conditions further comprises exposing at least a portion of the lower boiling product to the conversion catalyst under the conversion conditions.

Embodiment 4

The method of Embodiment 2 or 3, wherein the synthesis gas stream comprises 80 vol % or more of $H_2$ and CO.

Embodiment 5

The method of any of the above embodiments, wherein passing at least a portion of the solid particles comprising deposited coke from the reactor to the gasifier comprises passing the at least a portion of the solid particles comprising deposited coke to a heater, and passing the at least a portion of the solid particles comprising deposited coke from the heater to the gasifier.

Embodiment 6

The method of any of the above embodiments, wherein the first portion of partially gasified (or partially combusted) solid particles comprises a first weight percentage of metals (optionally a first combine weight percentage of Ni, V, Fe), relative to a weight of the first portion of partially gasified coke particles, that is greater than a weight percentage of metals (optionally a combined weight percentage of Ni, V, Fe) in the feedstock, relative to a weight of the feedstock.

Embodiment 7

The method of any of the above embodiments, wherein the exposing the at least a portion of the solid particles comprising deposited coke to gasification conditions (or coke combustion conditions) results in deposition of less than 0.1 wt % of metal oxides on a wall of the gasifier, relative to a metals content of the feedstock.

Embodiment 8

The method of any of the above embodiments, wherein passing at least a second portion of the partially gasified (or partially combusted) solid particles from the gasifier to the reactor comprises a) passing at least a second portion of the partially gasified solid particles from the gasifier to a coking section of the reactor; b) passing at least a second portion of the partially gasified solid particles from the gasifier to a stripping section of the reactor; or c) a combination of a) and b).

Embodiment 9

The method of any of the above embodiments, wherein the solid particles comprise coke particles.

Embodiment 10

The method of any of the above embodiments, where the at least a portion of the light ends product is exposed to the second portion of the partially gasified (or partially combusted) solid particles at a temperature of 500° C. to 750° C., or 600° C. to 700° C.

Embodiment 11

The method of any of the above embodiments, further comprising introducing an additional paraffin-containing stream into the second portion of the partially gasified solid particles after the second portion of the partially gasified solid particles exits from the gasifier and prior to passing the second portion of the partially gasified solid particles into the reactor.

Embodiment 12

An integrated fluidized coking system, comprising: a fluidized bed coker comprising a coker feed inlet, a cold coke outlet, at least one hot coke inlet, and a coker product outlet; a coke combustion reactor comprising: a coke combustion inlet in fluid communication with the cold coke outlet, a coke combustion outlet in fluid communication with the at least one hot coke inlet via at least one hot coke conduit, at least one coke combustion gas inlet, and a fuel gas outlet; a first separation stage comprising a first separation stage inlet in fluid communication with the coker product outlet, a first separation stage heavy product outlet and a first separation stage light ends outlet; and an oligomerization reactor comprising an oligomerization inlet in fluid communication with the first separation stage light ends outlet, an oligomerized product outlet, and an oligomerization light ends outlet in fluid communication with the at least one hot coke conduit, wherein optionally the coke combustion reactor comprises a gasifier, the at least one coke combustion gas inlet comprising at least one gasifier gas inlet.

Embodiment 13

An integrated fluidized coking system, comprising: a fluidized bed coker comprising a coker feed inlet, a cold coke outlet, at least one hot coke inlet, and a coker product outlet; a gasifier comprising: a gasifier coke inlet in fluid communication with the cold coke outlet, a gasifier coke outlet in fluid communication with the at least one hot coke inlet via at least one hot coke conduit, at least one gasifier input gas inlet, and a fuel gas outlet; a $CO_2$ separation stage comprising a separation stage inlet in fluid communication with the fuel gas outlet, a separation stage outlet in fluid communication with at least one gasifier input gas inlet, and a synthesis gas outlet; a methanol synthesis reactor comprising a synthesis gas inlet in fluid communication with the synthesis gas outlet and a methanol product outlet; and a methanol conversion stage comprising a conversion inlet in fluid communication with the methanol product outlet, a conversion stage heavy product outlet, and a conversion stage light ends outlet in fluid communication with the at least one hot coke conduit, the system optionally further comprising a first separation stage, the first separation stage comprising a first separation stage inlet in fluid communication with the coker product outlet, a first separation stage heavy product outlet and a first separation stage light ends outlet in fluid communication with the conversion inlet.

Embodiment 14

The system of any of Embodiments 12 to 13, further comprising a heater, the gasifier coke inlet being in indirect fluid communication with the cold coke outlet via the heater, the gasifier coke outlet being in indirect fluid communication with the at least one hot coke inlet via the heater.

Embodiment 15

The system of any of Embodiments 12 to 14, wherein the at least one hot coke inlet is in fluid communication with a coking section of the reactor, or wherein the at least one hot coke inlet is in fluid communication with a stripping section of the reactor, or a combination thereof.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for performing fluidized coking on a feed, comprising:
    exposing a feedstock comprising a T10 distillation point of 343° C. or more to a fluidized bed comprising solid particles in a reactor under coking conditions to form a coker effluent, the thermal cracking conditions comprising 10 wt % or more conversion of the feedstock relative to 343° C., the thermal cracking conditions being effective for depositing coke on the solid particles;
    introducing an oxygen-containing stream and steam into a coke combustion stage;
    passing at least a portion of the solid particles comprising deposited coke from the reactor to the coke combustion stage;
    exposing the at least a portion of the solid particles comprising deposited coke to combustion conditions to form a gas phase product comprising $H_2$, CO, and $CO_2$ and partially combusted solid particles;
    removing at least a first portion of the partially combusted solid particles from the coke combustion stage;
    passing at least a second portion of the partially combusted solid particles from the coke combustion stage to the reactor;
    separating the coker effluent to form a lower boiling product comprising $C_2$-$C_4$ olefins and a higher boiling product comprising a 343° C.– portion;
    exposing at least a portion of the lower boiling product to a catalyst under olefin oligomerization conditions to form an oligomerized product and a light ends product comprising $C_2$-$C_4$ paraffins; and
    introducing at least a portion of the light ends product into the second portion of the partially combusted solid particles after the second portion of the partially combusted solid particles exits from the coke combustion stage.

2. The method of claim 1, wherein the coke combustion stage comprises a gasifier.

3. The method of claim 1, wherein the at least a portion of the light ends product is introduced into the second portion of the partially combusted solid particles after the second portion of the partially combusted solid particles exits from the coke combustion stage and prior to passing the second portion of the partially combusted solid particles into the reactor.

4. The method of claim 1, where the at least a portion of the light ends product is exposed to the second portion of the partially gasified solid particles at a temperature of 500° C. to 750° C.

5. The method of claim 1, further comprising introducing an additional paraffin-containing stream into the second portion of the partially gasified solid particles after the second portion of the partially gasified solid particles exits from the gasifier and prior to passing the second portion of the partially gasified solid particles into the reactor.

6. A method for performing fluidized coking on a feed, comprising:
    exposing a feedstock comprising a T10 distillation point of 343° C. or more to a fluidized bed comprising solid particles in a reactor under coking conditions to form a coker effluent, the thermal cracking conditions comprising 10 wt % or more conversion of the feedstock relative to 343° C., the thermal cracking conditions being effective for depositing coke on the solid particles;

introducing an oxygen-containing stream and steam into a gasifier;

passing at least a portion of the solid particles comprising deposited coke from the reactor to the gasifier;

exposing the at least a portion of the solid particles comprising deposited coke to gasification conditions in a gasifier to form a gas phase product comprising $H_2$, CO, and $CO_2$ and partially gasified solid particles;

separating $CO_2$, $H_2S$, or a combination thereof from the gas phase product to form at least a synthesis gas stream;

exposing at least a portion of the synthesis gas stream to a methanol synthesis catalyst under synthesis conditions to form a methanol-containing product stream;

exposing at least a portion of the methanol-containing product stream to a conversion catalyst under conversion conditions to form a conversion product comprising $C_{5+}$ hydrocarbons and a light ends product comprising $C_2$-$C_4$ paraffins;

removing at least a first portion of the partially gasified solid particles from the gasifier;

passing at least a second portion of the partially gasified solid particles from the gasifier to the reactor; and introducing at least a portion of the light ends product into the second portion of the partially gasified solid particles after the second portion of the partially gasified solid particles exits from the gasifier and prior to passing the second portion of the partially gasified solid particles into the reactor.

7. The method of claim 6, further comprising separating the coker effluent to form a lower boiling product comprising $C_2$-$C_4$ olefins and a higher boiling product comprising a 343° C.– portion, wherein exposing at least a portion of the methanol-containing product stream to a conversion catalyst under conversion conditions further comprises exposing at least a portion of the lower boiling product to the conversion catalyst under the conversion conditions.

8. The method of claim 6, wherein the synthesis gas stream comprises 80 vol % or more of $H_2$ and CO.

9. The method of claim 6, wherein passing at least a portion of the solid particles comprising deposited coke from the reactor to the gasifier comprises passing the at least a portion of the solid particles comprising deposited coke to a heater, and passing the at least a portion of the solid particles comprising deposited coke from the heater to the gasifier.

10. The method of claim 6, wherein the first portion of partially gasified solid particles comprises a first weight percentage of metals, relative to a weight of the first portion of partially gasified coke particles, that is greater than a weight percentage of metals in the feedstock, relative to a weight of the feedstock.

11. The method of claim 6, wherein the exposing the at least a portion of the solid particles comprising deposited coke to gasification conditions results in deposition of less than 0.1 wt % of metal oxides on a wall of the gasifier, relative to a metals content of the feedstock.

12. The method of claim 6, wherein passing at least a second portion of the partially gasified solid particles from the gasifier to the reactor comprises a) passing at least a second portion of the partially gasified solid particles from the gasifier to a coking section of the reactor; b) passing at least a second portion of the partially gasified solid particles from the gasifier to a stripping section of the reactor; or c) a combination of a) and b).

13. The method of claim 6, wherein the solid particles comprise coke particles.

14. The method of claim 6, where the at least a portion of the light ends product is exposed to the second portion of the partially gasified solid particles at a temperature of 500° C. to 750° C.

15. The method of claim 6, further comprising introducing an additional paraffin-containing stream into the second portion of the partially gasified solid particles after the second portion of the partially gasified solid particles exits from the gasifier and prior to passing the second portion of the partially gasified solid particles into the reactor.

* * * * *